(12) United States Patent
Kjaer et al.

(10) Patent No.: US 8,232,242 B2
(45) Date of Patent: Jul. 31, 2012

(54) TREATMENT OF INFLAMMATORY BOWEL DISEASES WITH MAMMAL BETA DEFENSINS

(75) Inventors: Tanja Maria Rosenkilde Kjaer, Holte (DK); Thomas Kruse, Copenhagen N (DK); Per Holse Mygind, Vaerloese (DK); Karoline Sidelmann Brinch, Copenhagen NV (DK); Soeren Kjaerulff, Holte (DK); Birgitte Andersen, Bagsvaerd (DK)

(73) Assignee: Novozymes Adenium Biotech A/S, Bagsvaerd (DK)

(*) Notice: Subject to any disclaimer, the term of this patent is extended or adjusted under 35 U.S.C. 154(b) by 136 days.

(21) Appl. No.: 12/504,909

(22) Filed: Jul. 17, 2009

(65) Prior Publication Data

US 2010/0016230 A1 Jan. 21, 2010

Related U.S. Application Data

(60) Provisional application No. 61/086,910, filed on Aug. 7, 2008, provisional application No. 61/090,937, filed on Aug. 22, 2008, provisional application No. 61/094,556, filed on Sep. 5, 2008.

(30) Foreign Application Priority Data

| Jul. 18, 2008 | (EP) | 08160761 |
| Aug. 15, 2008 | (EP) | 08162486 |
| Sep. 3, 2008 | (EP) | 08163614 |

(51) Int. Cl.
*A61K 38/00* (2006.01)
*A61P 31/04* (2006.01)
(52) U.S. Cl. .......... 514/1.1; 514/2.3
(58) Field of Classification Search .......... None
See application file for complete search history.

(56) References Cited

U.S. PATENT DOCUMENTS

| 2006/0115480 A1 | 6/2006 | Hillman |
| 2008/0194481 A1 | 8/2008 | Rosen et al. |
| 2010/0016231 A1 | 1/2010 | Kjaer et al. |
| 2010/0016232 A1 | 1/2010 | Kjaer et al. |

FOREIGN PATENT DOCUMENTS

| WO | WO 2007/007116 A1 | 1/2007 |
| WO | WO 2007/081486 | 7/2007 |
| WO | WO 2007/081486 A2 | 7/2007 |
| WO | WO 2007/087557 | 8/2007 |
| WO | WO 2009/033776 A1 | 3/2009 |

OTHER PUBLICATIONS

Boniotto et al., Antimicrobiol Agents and Chemotheraphy, vol. 50, No. 4, pp. 1433-1441 (2006).
Bowdish et al., CTMI, vol. 306, pp. 27-66 (2006).
Gersemann et al., World Journal of Gastroentology, vol. 14, No. 36, pp. 5499-5503 (2008).
Lehrer, Nature Reviews Microbiology, vol. 2, pp. 727-738 (2004).
Niyonsaba et al., Journal of Investigative Dermatology, vol. 127, pp. 594-604 (2007).
Otte et al., Journal of Cellular Biochemistry, vol. 104, pp. 2286-2297 (2008).
Rowland et al., Immunopharmacology, vol. 40, pp. 11-20 (1998).
Schneider et al., J. Mol. Med., vol. 83, pp. 587-595 (2005).
Swidsinski et al., Gastroenterology, vol. 122, pp. 44-54 (2002).
Wehkamp et al., PNAS, vol. 102, No. 50, pp. 18129-18134 (2005).
Wehkamp et al., Inflammatory Bowel Diseases, vol. 9, No. 4, pp. 215-223 (2003).
Wehkamp et al., Journal of Leukocyte Biology, vol. 77, No. 4, pp. 460-465 (2005).
Wang et al., Expert Rev. Anti. Infect. Ther., vol. 5, No. 6, pp. 1049-1057 (2007).
Kawada et al., 2007, World Journal of Gastroenterology, vol. 13, No. 42, pp. 5581-5593.
Pazgier et al., 2006, Cellular and Molecular Life Sciences, vol. 63, pp. 1294-1313.
Rubbert-Roth et al., 2009, Arthritis Research and Therapy, vol. 11, pp. 1-12.
Wehkamp et al., 2002, European Journal of Gastroenterology & Hepatology, vol. 14, No. 7, pp. 745-752.
Wirtz et al., 2007, Advanced Drug Delivery Reviews vol. 59, pp. 1073-1083.
Aldhous, M.C., et al., "Dysregulation of Human β-defensin-2 Protein in Inflammatory Bowel Disease," *PLoS ONE* 4(7, article e6285) (2009).
Asadullah, K., et al., "IL-10 Is a Key Cytokine in Psoriasis. Proof of Principle by IL-10 Therapy: A New Therapeutic Approach," *J. Clin. Invest.* 101(4):783-794 (1998).
Berg, D.J., et al., "Enterocolitis and Colon Cancer in Interleukin-10-deficient Mice are Associated With Aberrant Cytokine Production and CD4+Th1-like Responses," *J Clin Invest*, 98:1010-20. (1996).
Bhavsar, M.D., and Amiji, M.M., "Oral IL-10 gene delivery in a microsphere-based formulation for local transfection and therapeutic efficacy in inflammatory bowel disease," *Gene Ther.* 15:1200-1209 (2008).
Chronnell, C.M.T., et. al., "Human β Defensin-1 and -2 Expression in Human Pilosebaceous Units: Upregulation in *Acne Vulgaris* Lesions," *J Invest. Dermatol.*, 117:1120-1125 (2001).
de Jongh, G.J., et. al., "High expression levels of keratinocyte antimicrobial proteins in psoriasis compared with atopic dermatitis," *J. Invest. Dermatol.*, 125: 1163-1173 (2005).
Duvallet E., et al., "A key cytokine in inflammatory diseases," *Annals of Medicine*, 43:503-511 (2011).
Fahlgren, A., et al., "Increased expression of antimicrobial peptides and lysozyme in colonic epithelial cells of patients with ulcerative colitis," *Clin Exp Immunol* 131:90-101 (2003).
Fedorak, R.N., et al., "Recombinant Human Interleukin 10 in the Treatment of Patients With Mild to Moderately Active Crohn's Disease," *Gastroenterology* 119:1473-1482 (2000).
Feldmann M., and Maini R.N., "TNF defined as a therapeutic target for rheumatoid arthritis and other autoimmune diseases," *Nat. Med.* 9(10):1245-1250. (2003).
Fellowes, R., et al., "Amelioration of established collagen induced arthritis by systemic IL-10 gene delivery," *Gene Ther.* 7: 967-977 (2000).
Finnegan, A., et al., "Collagen-induced arthritis is exacerbated in IL-10-deficient mice," *Arthritis Res. Ther.* 5(1): R18-R24 (2003).

(Continued)

*Primary Examiner* — Daniel C Gamett
(74) *Attorney, Agent, or Firm* — Hamilton, Brook, Smith & Reynolds, PC

(57) ABSTRACT

The present invention relates to treatment of inflammatory bowel diseases with mammal beta defensins.

8 Claims, No Drawings

OTHER PUBLICATIONS

Finnegan, A., et al., "Proteoglycan (aggrecan)-induced arthritis in BALB/c mice is a Th1-type disease regulated by Th2 cytokines," *J. Immunol.* 163: 5383-5390 (1999).

Gambichler, T., et al., "Expression of human β-defensins in patients with mycosis fungoides," *Arch Dermatol Res* 299: 221-224 (2007).

Jansen, P.A.M., et al., β-Defensin-2 Protein is a Serum Biomarker for Disease Activity in Psoriasis and Reaches Biologically Relevant Concentrations in Lesional Skin, *PLoS One* 4(3): e4725-e4725 (2009).

Kapel, N., et al., "Fecal β-Defensin-2 in Children With Inflammatory Bowel Diseases," *Journal of Pediatric Gastroenterology & Nutrition* 48:117-120 (2008).

Kasama, T., et al., "Interleukin-10 expression and chemokine regulation during the evolution of murine type II collagen-induced arthritis," *J. Clin. Invest.* 95: 2868-2876 (1995).

Lindsay J.O., et al., "Local delivery of adenoviral vectors encoding murine interleukin 10 induces colonic interleukin 10 production and is therapeutic for murine colitis," *Gut* 52:363-369 (2003).

Maini, R.N., et al. "rHUIL-10 in subjects with active rheumatoid arthritis (RA): A phase I and cytokine response study," *Arthritis Rheum.* 40:Abstract 1161, p. S224 (1997).

Mirandola S.R., et al., "Interferon-beta modifies the peripheral blood cell cytokine secretion in patients with multiple sclerosis," *Int Immunopharmacol* 9: 824-830 (2009).

Nakase H., et al., "New cytokine delivery system using gelatin microspheres containing interleukin-10 for experimental inflammatory bowel disease," *J Pharmacol Exp Ther* 301(1):59-65, (2002).

Özenci V, et al., "Multiple sclerosis is associated with an imbalance between tumour necrosis factor-alpha (TNF-α)- and IL-10-secreting blood cells that is corrected by interferon-beta (IFN-β) treatment," *Clin Exp Immunol* 120:147-153 (2000).

Schreiber, S., et al., "Safety and Efficacy of Recombinant Human Interleukin 10 in Chronic Active Crohn's Disease," *Gastroenterology* 119:1461-1472 (2000).

Singh, P.K., et al., "Production of β-defensins by human airway epithelia," *Proc. Natl. Acad. Sci. USA* 95:14961-14966 (1998).

Smeets, T.J.M., et al., "Analysis of serial synovial biopsies in patients with rheumatoid arthritis: description of a control group without clinical improvement after treatment with interleukin 10 or placebo," *J Rheumatol.* 26(10):2089-2093 (1999).

Steidler, L., et al., "Treatment of murine colitis by *Lactococcus lactis* secreting interleukin-10," *Science* 289:1352-1355 (2000).

van Roon, J.A.G., et al., "Interleukin 10 treatment of patients with rheumatoid arthritis enhances Fcγ receptor expression on monocytes and responsiveness to immune complex stimulation," *J Rheumatol.* 30(4):648-651 (2003).

Vordenbaumen, S., et al., "Elevated levels of human beta-defensin 2 and human neutrophil peptides in systemic lupus erythematosus," *Lupus* 19:1648-1653 (2010).

Walmsley M., et al., "Interleukin-10 inhibition of the progression of established collagen-induced arthritis," *Arthritis Rheum* 39(3):495-503 (1996).

Yudoh, K., et al., "Reduced expression of the regulatory CD4+ T cell subset is related to Th1/Th2 balance and disease severity in rheumatoid arthritis," *Arthritis Rheum* 43(3): 617-627 (2000).

Zhang, X., et al., "IL-10 is involved in the suppression of experimental autoimmune encephalomyelitis by $CD25^+CD4^+$ regulatory T cells," *Int Immunol* 16(2):249-256 (2003).

Office Action, U.S. Appl. No. 12/504,920, mailed Apr. 1, 2011.
Reply, U.S. Appl. No. 12/504,920, filed Jul. 28, 2011.
Final Office Action, U.S. Appl. No. 12/504,920, mailed Aug. 25, 2011.
Reply, U.S. Appl. No. 12/504,920, filed Dec. 22, 2011.
Office Action, U.S. Appl. No. 12/504,930, mailed Aug. 25, 2011.
Reply, U.S. Appl. No. 12/504,930, filed Dec. 22, 2011.

TREATMENT OF INFLAMMATORY BOWEL DISEASES WITH MAMMAL BETA DEFENSINS

CROSS-REFERENCE TO RELATED APPLICATIONS

This application claims priority or the benefit under 35 U.S.C. 119 of European application nos. EP08160761.6 filed Jul. 18, 2008, EP08162486.8 filed Aug. 15, 2008, and EP08163614.4 filed Sep. 3, 2008, and U.S. provisional application Nos. 61/086,910 filed Aug. 7, 2008, 61/090,937 filed Aug. 22, 2008, and 61/094,556 filed Sep. 5, 2008, the contents of which are fully incorporated herein by reference.

BACKGROUND OF THE INVENTION

1. Field of the Invention

The present invention relates to prevention and treatment of inflammatory bowel diseases by administration of a mammal beta defensin.

2. Background

Human Defensins

Among many other elements, key components of innate immunity are the antimicrobial peptides (AMPs) that individually show considerable selectivity, but collectively are able to rapidly kill a broad spectrum of bacteria, viruses and fungi. The biological significance of AMPs is emphasized by their ubiquitous distribution in nature and they are probably produced by all multicellular organisms. In humans the predominant AMPs are the defensins. The human defensins are small cationic peptides that can be divided into α- and β-defensins based on the topology of their three intramolecular cysteine disulphide bonds. The a-defensins can be further subdivided into those that were first isolated from neutrophil granules (HNP1-4) and those that are expressed by Paneth cells in the crypts of the small intestine (HD5 and HD6). The β-defensins are mainly produced by epithelial cells in various of tissues and organs including the skin, trachea, gastrointestinal tract, urogenital system, kidneys, pancreas and mammary gland. The best characterized members of the β-defensin family are hBD1-3. However, using various bioinformatics tools almost 40 open reading frames encoding putative β-defensin homologues have been annotated in the human genome. Some of the human defensins are produced constitutively, whereas others are induced by proinflammatory cytokines or exogenous microbial products.

It has become increasingly clear that the human defensins in addition to their direct antimicrobial activity also have a wide range of immunomodulatory/alternative properties. These include the induction of various chemokines and cytokines, chemotactic and apoptotic activities, induction of prostaglandin, histamine and leukotriene release, inhibition of complement, stimulation of dendritic cell maturation through toll-like receptor signaling and stimulation of pathogen clearance by neutrophils. Furthermore, the human defensins also play a role in wound healing, proliferation of epithelial and fibroblast cells, angiogenesis and vasculogenesis.

There is increasing evidence that the human defensins play an important role in many infectious and inflammatory diseases. Overexpression of human defensins is often observed in inflamed and/or infected skin most likely because of local induction by microbial components or endogenous proinflammatory cytokines. In psoriasis hBD2 and hBD3 are overabundant and in lesional epithelium of patients with acne vulgaris or superficial folliculitis a significant upregulation of hBD2 has been observed. On the other hand, downregulation of hBD2 and hBD3 has been associated with atopic dermatitis. Ileal Crohn's disease has been associated with deficient expression of HD5 and HD6 and in Crohn's disease in the colon expression of hBD2-4 are downregulated.

Cytokines

Cytokines are small, secreted polypeptides from higher eukaryotes which are responsible for intercellular signal transduction and which affect the growth, division and functions of other cells. They are potent, pleiotropic polypeptides that, e.g. via corresponding receptors, act as local or systemic intercellular regulatory factors, and therefore play crucial roles in many biologic processes, such as immunity, inflammation, and hematopoiesis. Cytokines are produced by diverse cell types including fibroblasts, endothelial cells, epithelial cells, macrophages/monocytes, and lymphocytes.

TNF-α is implicated in various pathophysiological processes and can be either protective, as in host defense, or deleterious, as in autoimmunity. TNF-α is one of the key cytokines that triggers and sustains the inflammation response and TNF-α inactivation has proven to be important in downregulating the inflammatory reactions associated with autoimmune diseases. Upon an infection, TNF-α is secreted in high amounts by macrophages and it mediates the recruitment of neutrophils and macrophages to sites of infection by stimulating endothelial cells to produce adhesion molecules and by producing chemokines, which are chemotactic cytokines. TNF-α help activate leukocytes and other inflammatory cells and increase vascular permeability within injured tissues. TNF-α is mainly produced by macrophages, monocytes and dendritic cells, but also by a broad variety of other cell types including lymphoid cells, mast cells, endothelial cells, cardiac myocytes, adipose tissue, fibroblasts and neuronal tissue.

Current anti-inflammatory drugs block the action of TNF-α by binding to it and hereby prevents it from signaling the receptors for TNF-α on the surface of cells. This type of blocking has some serious side effects, of which some is infections such as tuberculosis, sepsis and fungal infections and possible increased cancer incidence.

IL-10, also known as human cytokine synthesis inhibitory factor (CSIF), is also a key 5 player in immune regulation as an anti-inflammatory cytokine. This cytokine is produced by several cell types including monocytes, macrophages, T cells, B cells, dendritic cells and mast cells. This cytokine has pleiotropic effects in immunoregulation and inflammation. It down-regulates the expression of pro-inflammatory cytokines, cytokines secreted by Th1/Th17 cells, MHC class II Ags, and costimulatory molecules on antigen-presenting cells. IL-10 is also secreted by a population of T cells called regulatory T cells (Tregs). These cells do not prevent initial T cell activation; rather, they inhibit a sustained response and prevent chronic and potentially damaging responses. In the periphery some T cells are induced to become Tregs by antigen and either IL-10 or TGF-β. Tregs induced by IL-10 are CD4+/CD25+/Foxp3—and are referred to as Tr1 cells. These cells suppress immune responses by secretion of IL-10. Recent studies have revealed a greater diversification of the T cell effector repertoire than the Th1/Th2/Treg with the identification of Th17 cells. This subpopulation has been shown to be pathogenic in several autoimmune diseases, such as Crohn's disease, ulcerative colitis, psoriasis and multiple scelerosis, previously attributed to the Th1 lineage. The cytokines secreted by Th17 are also downregulated by IL-10 and blocking of TNF prevents psoriasis by inactivating Th17 cells. The overall activity of IL-10 is anti-inflammatory and it has been shown to prevent inflammation and injury in several animal studies, however clinical IL-10 treatment remains insufficient because of difficulties in the route of IL-10 administration and its biological half-life.

Inflammatory Bowel Diseases

Inflammatory bowel diseases (IBD) are defined by chronic, relapsing intestinal inflammation of obscure origin. IBD refers to two distinct disorders, Crohn's disease and ulcerative colitis (UC). Both diseases appear to result from the unrestrained activation of an inflammatory response in the intestine. This inflammatory cascade is thought to be perpetuated through the actions of proinflammatory cytokines and selective activation of lymphocyte subsets. In patients with IBD, ulcers and inflammation of the inner lining of the intestines lead to symptoms of abdominal pain, diarrhea, and rectal bleeding. Ulcerative colitis occurs in the large intestine, while in Crohn's, the disease can involve the entire GI tract as well as the small and large intestines. For most patients, IBD is a chronic condition with symptoms lasting for months to years. It is most common in young adults, but can occur at any age. It is found worldwide, but is most common in industrialized countries such as the United States, England, and northern Europe. It is especially common in people of Jewish descent and has racial differences in incidence as well. The clinical symptoms of IBD are intermittent rectal bleeding, crampy abdominal pain, weight loss and diarrhea. Diagnosis of IBD is based on the clinical symptoms, the use of a barium enema, but direct visualization (sigmoidoscopy or colonoscopy) is the most accurate test. Protracted IBD is a risk factor for colon cancer, and treatment of IBD can involve medications and surgery.

Some patients with UC only have disease in the rectum (proctitis). Others with UC have disease limited to the rectum and the adjacent left colon (proctosigmoiditis). Yet others have UC of the entire colon (universal IBD). Symptoms of UC are generally more severe with more extensive disease (larger portion of the colon involved with disease).

The prognosis for patients with disease limited to the rectum (proctitis) or UC limited to the end of the left colon (proctosigmoiditis) is better then that of full colon UC. Brief periodic treatments using oral medications or enemas may be sufficient. In those with more extensive disease, blood loss from the inflamed intestines can lead to anemia, and may require treatment with iron supplements or even blood transfusions. Rarely, the colon can acutely dilate to a large size when the inflammation becomes very severe. This condition is called toxic megacolon. Patients with toxic megacolon are extremely ill with fever, abdominal pain and distention, dehydration, and malnutrition. Unless the patient improves rapidly with medication, surgery is usually necessary to prevent colon rupture.

Crohn's disease can occur in all regions of the gastrointestinal tract. With this disease intestinal obstruction due to inflammation and fibrosis occurs in a large number of patients. Granulomas and fistula formation are frequent complications of Crohn's disease. Disease progression consequences include intravenous feeding, surgery and colostomy.

IBD may be treated medicinally. The most commonly used medications to treat IBD are anti-inflammatory drugs such as the salicylates. The salicylate preparations have been effective in treating mild to moderate disease. They can also decrease the frequency of disease flares when the medications are taken on a prolonged basis. Examples of salicylates include sulfasalazine, olsalazine, and mesalamine. All of these medications are given orally in high doses for maximal therapeutic benefit. These medicines are not without side effects. Azulfidine can cause upset stomach when taken in high doses, and rare cases of mild kidney inflammation have been reported with some salicylate preparations.

Corticosteroids are more potent and faster-acting than salicylates in the treatment of IBD, but potentially serious side effects limit the use of corticosteroids to patients with more severe disease. Side effects of corticosteroids usually occur with long term use. They include thinning of the bone and skin, infections, diabetes, muscle wasting, rounding of faces, psychiatric disturbances, and, on rare occasions, destruction of hip joints.

In IBD patients that do not respond to salicylates or corticosteroids, medications that suppress the immune system are used. Examples of immunosuppressants include azathioprine and 6-mercaptopurine. Immunosuppressants used in this situation help to control IBD and allow gradual reduction or elimination of corticosteroids. However, immunosuppressants render the patient immuno-compromised and susceptible to many other diseases.

A well recognized model for studying IBD is the DSS colitis mouse model, as described in Kawada et al. "Insights from advances in research of chemically induced experimental models of human inflammatory bowel disease", World J. Gastroenterol., Vol. 13 (42), pp. 5581-5593 (2007); and Wirtz and Neurath "Mouse models of inflammatory bowel disease", Advanced Drug Delivery Reviews, Vol. 59 (11), 1073-1083 (2007).

Clearly there is a great need for agents capable of preventing and treating IBD.

Using Human Defensins to treat Inflammatory Bowel Diseases

Interestingly, Crohn's disease in the small intestine has been associated with decreased levels of the paneth cell α-defensins HD5 and HD6, whereas Crohn's disease in the colon has been associated with reduced production of the β-defensins hBD2 and hBD3 (Gersemann et al., 2008; Wehkamp et al, 2005). Furthermore, involvement of the enteric microbiota in the pathogenesis of Crohn's has been convincingly demonstrated (Swidsinski et al., 2002). Using fluorescence in situ hybridization, these researchers showed that in active Crohn's disease a drastic increase of mucosa-associated and invasive bacteria was observed, whereas these bacteria are absent from the normal small and large bowel epithelium. Together these observations have merged into a hypothesis, which suggest that in healthy persons a proper level of defensins along the intestinal epithelial barrier acts to control the composition and number of luminal bacteria and keep them away from adhering to and invading the mucosa to trigger an inflammation (Wang et al., 2007). On the other hand, in persons with an insufficient ability to produce a protective level of secreted defensins, the balance is shifted between the antimicrobial defence and the luminal bacteria. As a result, this allows a bacterial invasion into underlying intestinal tissues that induce an inflammatory state, which in turn, may develop into Crohn's disease.

Based on this hypothesis, WO 2007/081486 discloses the use of several human defensins in the treatment of inflammatory bowel disease. The inventors suggested that defensins administered orally to Crohn's patients, in a formulation that allow their release at proper locations in the intestinal lumen, would reduce the number of invading bacteria, re-establish a normal epithelial barrier function and, thus, reduce the severity of the inflammatory disease.

According to WO 2007/081486, the function of the defensins is to directly target and kill bacteria in the lumen to prevent them from invading the epithelial tissue. That is, the function of the defensins is purely as an anti-infective compound. In relation to WO/2007/081486, it is surprising that hBD2 administered parentally is able to reduce the severity of DSS induced colitis in mice, because by using this route of administration the peptide never encounters luminal bacteria. Additionally, we show here that the effect of hBD2 is a reduction of the level of the pro-inflammatory cytokines TNFα, IL-1 and IL-23 secreted by PBMCs. These cytokines are known to be key players in many inflammatory diseases including inflammatory bowel disease. It has been known for more than a decade that the defensins beside their anti-microbial functions also posses a range of immunomodulatory functions. However, the large majority of work on the immune modulating properties of the human defensins describes them as having primarily pro-inflammatory or immune enhancing functions (See for example, Niyonsaba et al., 2007; Bowdish et al., 2006; Lehrer, 2004).

Hence, it is truly unexpected that hBD2 administered parentally should be able to reduce disease severity in IBD patients. First of all, when administered parentally, hBD2 would never reach the intestinal lumen to encounter harmful bacteria involved in inducing the disease. Moreover, based on the large majority of published literature, one would expect that a defensin entering the blood stream would induce a pro-inflammatory rather than an anti-inflammatory response, as observed in the work presented here.

DETAILED DESCRIPTION OF THE INVENTION

Definitions

Defensin: The term "defensin" as used herein refers to polypeptides recognized by a person skilled in the art as belonging to the defensin class of antimicrobial peptides. To determine if a polypeptide is a defensin according to the invention, the amino acid sequence may be compared with the hidden markov model profiles (HMM profiles) of the PFAM database by using the freely available HMMER software package.

The PFAM defensin families include for example Defensin_1 or "Mammalian defensin" (accession no. PF00323), and Defensin_2 or Defensin_beta or "Beta Defensin" (accession no. PF00711).

The defensins of the invention belong to the beta defensin class. The defensins from the beta defensin class share common structural features, such as the cysteine pattern.

Examples of defensins, according to the invention, include human beta defensin 1 (hBD1; see SEQ ID NO:1), human beta defensin 2 (hBD2; see SEQ ID NO:2), human beta defensin 3 (hBD3; see SEQ ID NO:3), human beta defensin 4 (hBD4; see SEQ ID NO:4), and mouse beta defensin 3 (mBD3; see SEQ ID NO:6).

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues ×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; http://emboss.org), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment).

Isolated polypeptide: The term "isolated variant" or "isolated polypeptide" as used herein refers to a variant or a polypeptide that is isolated from a source. In one aspect, the variant or polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Mammal Beta Defensins

The present invention relates to pharmaceutical uses of mammal beta defensins, such as human beta defensins and/or mouse beta defensins, in the treatment of inflammatory bowel diseases, such as ulcerative colitis and/or Crohns disease. The treatment is preferably associated with reduced TNF-alpha activity in treated tissues.

In an embodiment, the mammal beta defensins of the invention have a degree of identity of at least 80%, preferably at least 85%, more preferably at least 90%, and most preferably at least 95% to any of the amino acid sequences of SEQ ID NO:1, SEQ ID NO:2, SEQ ID NO:3, SEQ ID NO:4, SEQ ID NO:5 and/or SEQ ID NO:6. In a preferred embodiment, the mammal beta defensins of the invention have a degree of identity of at least 80%, preferably at least 85%, more preferably at least 90%, and most preferably at least 95% to any of the amino acid sequences of SEQ ID NO:1, SEQ ID NO:2, SEQ ID NO:3 and/or SEQ ID NO:4. In a more preferred embodiment, the mammal beta defensins of the invention consist of human beta defensin 1 (SEQ ID NO:1), human beta defensin 2 (SEQ ID NO:2), human beta defensin 3 (SEQ ID NO:3), human beta defensin 4 (SEQ ID NO:4), a variant of human beta defensin 4 (SEQ ID NO:5) and/or mouse beta defensin 3 (SEQ ID NO:6). In an even more preferred embodiment, the mammal beta defensins of the invention consist of human beta defensin 1 (SEQ ID NO:1), human beta defensin 2 (SEQ ID NO:2), human beta defensin 3 (SEQ ID NO:3) and/or human beta defensin 4 (SEQ ID NO:4).

In another embodiment, the mammal beta defensins of the invention have a degree of identity of at least 80%, preferably at least 85%, more preferably at least 90%, and most preferably at least 95% to the amino acid sequence of SEQ ID NO:2. In a preferred embodiment, the mammal beta defensins of the invention consist of human beta defensin 2 (SEQ ID NO:2).

In yet another embodiment, the mammal beta defensins of the invention consist of human beta defensins and/or mouse beta defensins, and functionally equivalent variants thereof. Preferably, the mammal beta defensins consist of human beta defensin 1, human beta defensin 2, human beta defensin 3, human beta defensin 4 and mouse beta defensin 3, and functionally equivalent variants thereof. More preferably, the mammal beta defensins of the invention consist of human beta defensin 2, and functionally equivalent variants thereof.

The mammal beta defensins of the invention are also referred to as compounds of the preferred embodiments.

In the context of the present invention, a "functionally equivalent variant" of a mammal (e.g. human) beta defensin is a modified mammal (e.g. human) beta defensin exhibiting approx. the same effect on an inflammatory bowel disease as the parent mammal (e.g. human) beta defensin. Preferably, it also exhibits approx. the same effect on TNF-alpha activity as the mammal (e.g. human) beta defensin.

According to the invention, a functionally equivalent variant of a mammal (e.g. human) beta defensin may comprise 1-5 amino acid modifications, preferably 1-4 amino acid modifications, more preferably 1-3 amino acid modifications, most preferably 1-2 amino acid modification(s), and in particular one amino acid modification, as compared to the mammal (e.g. human) beta defensin amino acid sequence.

The term "modification" means herein any chemical modification of a mammal (e.g. human) beta defensin. The modification(s) can be substitution(s), deletion(s) and/or insertions (s) of the amino acid(s) as well as replacement(s) of amino acid side chain(s); or use of unnatural amino acids with similar characteristics in the amino acid sequence. In particular the modification(s) can be amidations, such as amidation of the C-terminus.

Preferably, amino acid modifications are of a minor nature, that is conservative amino acid substitutions or insertions that do not significantly affect the folding and/or activity of the polypeptide; single deletions; small amino- or carboxyl-terminal extensions; a small linker peptide of up to about 20-25 residues; or a small extension that facilitates purification by changing net charge or another function, such as a polyhistidine tag, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in a mammal beta defensin can be identified according to procedures known in the art, such as site-directed mutagenesis or alanine-scanning mutagenesis (Cunningham and Wells, 1989, $Science$ 244: 1081-1085). In the latter technique, single alanine mutations are introduced at every residue in the molecule, and the resultant mutant molecules are tested for biological activity (i.e., activity against an inflammatory bowel disease and/or suppresion of TNF-alpha activity) to identify amino acid residues that are critical to the activity of the molecule. See also, Hilton et al., 1996, $J. Biol. Chem.$ 271: 4699-4708. The identities of essential amino acids can also be inferred from analysis of identities with polypeptides which are related to mammal beta defensins.

Single or multiple amino acid substitutions can be made and tested using known methods of mutagenesis, recombination, and/or shuffling, followed by a relevant screening procedure, such as those disclosed by Reidhaar-Olson and Sauer, 1988, $Science$ 241: 53-57; Bowie and Sauer, 1989, $Proc. Natl. Acad. Sci. USA$ 86: 2152-2156; WO 95/17413; or WO 95/22625. Other methods that can be used include error-prone PCR, phage display (e.g., Lowman et al., 1991, $Biochem.$ 30:10832-10837; U.S. Pat. No. 5,223,409; WO 92/06204), and region-directed mutagenesis (Derbyshire et al., 1986, $Gene$ 46:145; Ner et al., 1988, $DNA$ 7:127).

An N-terminal extension of the polypeptides of the invention may suitably consist of from 1 to 50 amino acids, preferably 2-20 amino acids, especially 3-15 amino acids. In one embodiment N-terminal peptide extension does not contain an Arg (R). In another embodiment the N-terminal extension comprises a kex2 or kex2-like cleavage site as will be defined further below. In a preferred embodiment the N-terminal extension is a peptide, comprising at least two Glu (E) and/or Asp (D) amino acid residues, such as an N-terminal extension comprising one of the following sequences: EAE, EE, DE and DD.

Methods and Uses

Human beta defensin 2 was found to significantly reduce the severity of disease parameters in a 10-Day Dextran Sodium Sulphate (DSS)-induced colitis model in the mouse; thus showing potent activity as a medicament for treatment of inflammatory bowel diseases, such as ulcerative colitis and Chrohn's disease.

The present invention therefore provides methods of treating inflammatory bowel diseases, which treatment comprises administering parenterally to a subject in need of such treatment an effective amount of a mammal beta defensin, such as human beta defensin 2, e.g., in the form of a pharmaceutical composition. Also provided are mammal beta defensins, such as human beta defensin 2, for the manufacture of a medicament for parenteral administration, and the use of mammal beta defensins, such as human beta defensin 2, for the manufacture of a medicament for parenteral administration, e.g., a pharmaceutical composition, for the treatment of inflammatory bowel disease. Treatment includes treatment of an existing disease or disorder, as well as prophylaxis (prevention) of a disease or disorder.

In an embodiment, the treatment results in reduced TNF-alpha activity in treated tissues, preferably reduced TNF-alpha activity and increased IL-10 activity.

Mammal beta defensins can be employed therapeutically in compositions formulated for administration by any conventional route, including enterally (e.g., buccal, oral, nasal, rectal), parenterally (e.g., intravenous, intracranial, intraperitoneal, subcutaneous, or intramuscular), or topically (e.g., epicutaneous, intranasal, or intratracheal). Within other embodiments, the compositions described herein may be administered as part of a sustained release implant.

Within yet other embodiments, compositions of preferred embodiments may be formulized as a lyophilizate, utilizing appropriate excipients that provide stability as a lyophilizate, and subsequent to rehydration.

Pharmaceutical compositions containing a mammal beta defensin, such as a human beta defensin, can be manufactured according to conventional methods, e.g., by mixing, granulating, coating, dissolving or lyophilizing processes.

Pharmaceutical compositions of preferred embodiments comprise a mammal beta defensin, such as a human beta defensin, and a pharmaceutically acceptable carrier and/or diluent.

A mammal beta defensin, such as a human beta defensin, is preferably employed in pharmaceutical compositions in an amount which is effective to treat an inflammatory bowel disease, preferably with acceptable toxicity to the patient. For such treatment, the appropriate dosage will, of course, vary depending upon, for example, the chemical nature and the pharmacokinetic data of a compound of the present invention used, the individual host, the mode of administration and the nature and severity of the conditions being treated. However, in general, for satisfactory results in larger mammals, for example humans, an indicated daily dosage is preferably from about 0.001 g to about 1.5 g, more preferably from about 0.01 g to 1.0 g; or from about 0.001 mg/kg body weight to about 20 mg/kg body weight, preferably from about 0.01 mg/kg body weight to about 20 mg/kg body weight, more preferably from about 0.1 mg/kg body weight to about 10 mg/kg body weight, for example, administered in divided doses up to one, two, three, or four times a day. The compounds of preferred embodiments can be administered to larger mammals, for example humans, by similar modes of administration at similar dosages than conventionally used.

In certain embodiments, the pharmaceutical compositions of preferred embodiments can include a mammal beta defensin, such as a human beta defensin, in an amount of about 0.5 mg or less to about 1500 mg or more per unit dosage form depending upon the route of administration, preferably from about 0.5, 0.6, 0.7, 0.8, or 0.9 mg to about 150, 200, 250, 300, 350, 400, 450, 500, 600, 700, 800, 900, or 1000 mg, and more preferably from about 1, 2, 3, 4, 5, 6, 7, 8, 9, 10, 15, 20, or 25 mg to about 30, 35, 40, 45, 50, 55, 60, 65, 70, 75, 80, 85, 90, 95, or 100 mg. In certain embodiments, however, lower or higher dosages than those mentioned above may be preferred. Appropriate concentrations and dosages can be readily determined by one skilled in the art.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats, and other common additives. The compositions can also be formulated as pills, capsules, granules, tablets (coated or uncoated), (injectable) solutions, solid solutions, suspensions, dispersions, solid dispersions (e.g., in the form of ampoules, vials, creams, gels, pastes, inhaler powder, foams, tinctures, lipsticks, drops, sprays, or suppositories). The formulation can contain (in addition to a mammal beta defensin, and other optional active ingredients) carriers, fillers, disintegrators, flow conditioners, sugars and sweeteners, fragrances, preservatives, stabilizers, wetting agents, emulsifiers, solubilizers, salts for regulating osmotic pressure, buffers, diluents, dispersing and surface-active agents, binders, lubricants, and/or other pharmaceutical excipients as are known in the art. One skilled in this art may further formulate mammal beta defensins in an appropriate manner, and in accordance with accepted practices, such as those described in Remington's Pharmaceutical Sciences, Gennaro, Ed., Mack Publishing Co., Easton, Pa. 1990.

A mammal beta defensin, such as a human beta defensin, can be used alone, or in combination therapies with one, two, or more other pharmaceutical compounds or drug substances, and/or with one or more pharmaceutically acceptable excipient(s).

In vitro Synthesis

Mammal beta defensins may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Mammal beta defensins, or functional equivalents thereof, may also be isolated and purified in accordance with conventional methods of recombinant synthesis. A lysate may be prepared of the expression host and the lysate purified using HPLC, exclusion chromatography, gel electrophoresis, affinity chromatography, or other purification technique.

The present invention is further described by the following examples that should not be construed as limiting the scope of the invention.

EXAMPLES

During testing of hBD2 for immunomodulatory effects it was unexpectedly observed that hBD2 had vast anti-inflammatory potential.

Here, we have shown that hBD2 has significant effect in treating inflammatory bowel disease (colitis) induced by oral dextran sodium sulphate (DSS) administration in the mouse. We have also shown that hBD2 has downregulating potential on TNF-alpha.

Example 1

Production of Human Beta Defensin 2 (hBD2)

hBD2 was produced recombinantly. A synthetic DNA fragment (DNA 2.0) encoding hBD2 was cloned into the pET-32(+) expression vector (Novagen). The resulting plasmid encoded a translational fusion peptide containing an N-terminal thioredoxin part followed by a his-tag, an enterokinase cleavage site and finally the hBD2 peptide. The expression plasmid was transformed into *E. coli* strain BL21.

An overnight culture of this strain was diluted 100 fold in TB-glycerol containing 100 pg/ml of ampicillin and grown to an OD600 of approximately 8 at 37° C. and induced with 0.5 mM of IPTG for 3 hours after which the cells were harvested by centrifugation. The his-tagged trx-hBD2 fusion peptide was purified on Ni-NTA beads (QIAGEN) using standard protocols. The his-tag purified fusion peptide was subsequently dialysed over-night into enterokinase buffer (50 mM tris-HCl pH 7.5, 1 mM $CaCl_2$) and cleaved with enterokinase to release mature hBD2. The hBD2 peptide was further purified by cation-exchange chromatography using Source 15 S matrix (Amersham Biosciences). The correct molecular weight of hBD2 was verified using MALDI-TOF mass spectrometry.

Production of mBD3 (see Example 7) was carried out using an identical protocol.

The proper folding and disulphide-bridge topology of the hBD2 molecule was subsequently verified using tryptic digestion coupled with LC-MS and NMR spectroscopy.

Endotoxin was removed by preparative RP-HPLC at low pH, and the content of endotoxin was determined by a LAL assay (Endosafe KTA2) and the level was found to be below the detection limit of the assay (0.05 EU/mg). To ascertain that levels below the detection limit of the endotoxin assay were not able to stimulate PBMC, titration curves of stimulation with a very potent lipopolysaccharide (*E. coli*, 0111:B4, Sigma L4391) were performed. Very low levels of this LPS (0.06 ng/ml) were able to stimulate PBMC to a detectable cytokine production.

Example 2

10-Day Dextran Sodium Sulphate (DSS)-induced Colitis Model in the Mouse

The aim of the following study was to determine the anti-inflammatory activity of human beta defensin 2 in an acute (10-days) model of inflammatory bowel disease (colitis) induced by oral dextran sodium sulphate (DSS) administration in the mouse.

The DSS colitis mouse model is a well recognized model for studying inflammatory bowel disease, as described in Kawada et al. "Insights from advances in research of chemically induced experimental models of human inflammatory bowel disease", World J. Gastroenterol., Vol. 13 (42), pp. 5581-5593 (2007); and Wirtz and Neurath "Mouse models of inflammatory bowel disease", Advanced Drug Delivery Reviews, Vol. 59 (11), 1073-1083 (2007).

Materials
Test Items
Human beta defensin 2 (hBD2); see Example 1 above
Methylprednisolone 21-hemisuccinate ("prednisolone")
PBS buffer (GIBCO)
Experimental Animals Male C57BL/6 mice (Harlan Interfauna Ibérica, Barcelona, Spain) were used in the study, as this is a species and sex that has been demonstrated to develop significant inflammation of the colon when administered a 2% solution of DSS in the drinking water over a period of 10 days.

Identification

Animals were identified by number and letter codes on their tails. Additionally, each cage was identified by a colour-coded card indicating the number and sex of the animals, the test item code or name, dose level, administration route, treatment period, group number, study code and study director's name.

Weight

The average body weight of the animals on the day of start of the study was 22.4±0.16 g Acclimatization (Quarantine)

Minimum of 7 days prior to the start of the study, under the same conditions as those of the main study.

Housing

On arrival, the animals were separated and housed at random in policarbonate cages (E-Type, Charles River, 255× 405×197mm) with stainless steel lids.

Animals were housed in groups of five animals per cage according to their sex, in animal rooms with controlled temperature (22±2° C.), lighting (12/12 hours light/darkness), air pressure, number of air renovations and relative humidity (30-70%).

The cages all had sawdust (Lignocel 3-4; Harlan Interfauna Ibérica, Spain) on the floor as litter.

Food and water

All mice had free access to a dry, pelleted standard rodent diet (Teklad Global 2014; Harlan Interfauna Ibérica, Spain).

Water was provided ad libitum in bottles. Tap water supply to the animal rooms is periodically analysed to check its composition and to detect possible contaminants (chemical and microbiological).

Equipment and Materials
Equipment:
  Animal balance Sartorius Mod. BP 2100
  Surgical dissection equipment
  Eppendorf 5415 C centrifuge
  Nikon Eclipse E600FN microscope
  Hook & Tucker instruments rotamixer
  IKA Ultra Turrax Homogeniser
  Sartorius Mod. BP 221S analytical balance
  ELISA microplate reader Labsystems Multiskan EX
Materials and Reagents:
  Sterile disposable syringes (1 ml)
  Sterile Butterfly 25 G infusion set
  Anaesthetic (Ketamine/Xylazine)
  Topical Anaesthetic cream (EMLA, Astra Zeneca)
  Dextran Sodium Sulphate 30.000-50.000 Da (MP Biomedicals)
  Phosphate Buffered Saline (PBS; Sigma)
  Neutral Buffered Formalin (VWR)
  Bovine Serum Albumin (Sigma)
  Protease Inhibitor Cocktail (Sigma)
  Mouse TNF-α ELISA kit (GE Healthcare)
Experimental Protocol
Study design Animals were divided into 5 experimental groups. Each group consisted of 10 males:
Group A: Treated with Control vehicle (PBS) i.v.
Group B: Treated with hBD2 (0.1 mg/kg i.v.)
Group C: Treated with hBD2 (1 mg/kg i.v.)
Group D: Treated with hBD2 (10 mg/kg i.v.)
Group E: Treated with methylprednisolone (1 mg/kg p.o.)

Animal allocation to all experimental groups was done in a randomized manner. A maximum of 5 mice were housed in each cage (as per Directive 86/609/EEC). All animals were weighed on their arrival at the laboratory and prior to the administration of the test items.

Administration of the Test Substance

The control vehicle and hBD2 were administered intravenously via the tail vein with the use of a sterile needle (25G) in a dosing volume of 5 ml/kg body weight as a slow bolus. The animals received one dose daily (every 24 hours) of the corresponding test item (hBD2, prednisolone or control vehicle) for 10 consecutive days.

Prednisolone was given orally at a dose of 1 mg/kg in a dosing volume of 5 ml/kg body weight, in the same dosing regime as hBD2.

Experimental Procedure

Induction of Colitis

Colitis was induced in mice by supplementing their drinking water with DSS 2% for 7 days.

On Day 1 all mice were weighed and marked according to their experimental groups. The drinking bottle of each cage was filled with the DSS solution, making sure all bottle lids were mounted properly and that none were congested.

On Day 3 any remaining solution in the bottles was emptied and refilled with fresh DSS solution. This procedure was repeated again on Day 5.

On Day 8 any remaining solution was discarded and replaced with autoclaved water. Animals were sacrificed 2 days later on Day 10.

Clinical Assessment (Disease Activity Index)

Daily clinical assessment of DSS-treated animals was carried out, with the calculation of a validated clinical Disease Activity Index (DAI) ranging from 0 to 4 according to the following parameters: stool consistency, presence or absence of rectal bleeding and weight loss:

| Parameter | | DAI score |
|---|---|---|
| Change in Body Weight: | <1% | 0 |
| | 1-5% | 1 |
| | 5-10% | 2 |
| | 10-15% | 3 |
| | >15% | 4 |
| Rectal Bleeding: | Negative | 0 |
| | Positive | 4 |
| Stool Consistency: | Normal | 0 |
| | Loose Stools | 2 |
| | Diarrhoea | 4 |

Bodyweight loss was calculated as the percent difference between the original bodyweight (Day 1) and the actual bodyweight on each experimental day (2-10).

The appearance of diarrhoea is defined as mucus/faecal material adherent to anal fur. Rectal bleeding is defined as diarrhoea containing visible blood/mucus or gross rectal bleeding. The maximum score of the DAI each day is 12.

Blood Sampling

Two blood samples were obtained from each animal on two separate occasions during the course of the study: on Day 1 and on Day 5. Blood samples were obtained on each occasion into Microvette CB-300 microtubes by puncture of the saphenous vein 2 hours after administration of the test item. This blood extraction method does not require anaesthetic or analgesics and produces a minimum stress in the animals (Hem et al., 1998). Additionally a terminal blood sample was obtained from all animals on the last day of the study from the abdominal vena cava also two hours after test item administration.

Blood samples were allowed to clot and then centrifuged at 3000 rpm for 10 min and the resulting serum frozen at -80° C. for storage.

Euthanasia and Collection of Colon Samples

On day 10, two hours after the last administration of control vehicle, hBD2 or prednisolone, the animals were killed by an overdose of anaesthetic. Their colons were removed and their length and weight measured after exclusion of the caecum.

Two sections (proximal and distal) of colon were taken from each animal and preserved in neutral buffered formalin for subsequent histological analysis (haematoxylin and eosin staining) according to the following scoring system:

| Description | Score |
|---|---|
| No changes observed | 0 |
| Minimal scattered mucosal inflammatory cell infiltrates, with or without minimal epithelial hyperplasia. | 1 |
| Mild scattered to diffuse inflammatory cell infiltrates, sometimes extending into the submucosa and associated with erosions, with minimal to mild epithelial hyperplasia and minimal to mild mucin depletion from goblet cells. | 2 |
| Mild to moderate inflammatory cell infiltrates that were sometimes transmural, often associated with ulceration, with moderate epithelial hyperplasia and mucin depletion. | 3 |
| Marked inflammatory cell infiltrates that were often transmural and associated with ulceration, with marked epithelial hyperplasia and mucin depletion. | 4 |
| Marked transmural inflammation with severe ulceration and loss of intestinal glands. | 5 |

Determination of TNF-alpha Concentration in Colonic Tissue Samples

An additional sample of colon was obtained from each animal and homogenised in PBS (100 mg tissue/ml PBS) containing 1% bovine serum albumin (BSA) and a protease inhibitor cocktail (1 ml/20 g tissue). The homogenate was then be centrifuged at 1400 rpm for 10 min and the supernatant stored at −20° C. for subsequent determination of TNF-α concentration by specific enzyme immunoassay (ELISA).

Results

Disease Activity Index Score

TABLE 1

Disease Activity Index (DAI) score progression during Day 1 to Day 10. Significant differences from control (vehicle) group values at a given date are shown as *p < 0.05; **p < 0.01 (Kruskal-Wallis Test for non-parametric data).

| Test item | Data | DAI score | | | | |
|---|---|---|---|---|---|---|
| | | Day 1 | Day 2 | Day 3 | Day 4 | Day 5 |
| Group A | Mean | 0.00 | 1.10 | 1.30 | 3.20 | 2.90 |
| Control vehicle i.v. | S.E.M. | 0.00 | 0.31 | 0.37 | 0.36 | 0.31 |
| Group B | Mean | 0.00 | 0.20 | 0.80 | 2.90 | 2.80 |
| hBD2 0.1 mg/kg i.v. | S.E.M. | 0.00 | 0.13 | 0.20 | 0.10 | 0.13 |
| Group C | Mean | 0.00 | 0.00 | 0.22 | 2.22 | 2.44 |
| hBD2 1 mg/kg i.v. | S.E.M. | 0.00 | 0.00 | 0.22 | 0.15 | 0.18 |
| Group D | Mean | 0.00 | 0.60 | 1.00 | 3.67 | 3.11 |
| hBD2 10 mg/kg i.v. | S.E.M. | 0.00 | 0.22 | 0.44 | 0.24 | 0.26 |
| Group E | Mean | 0.00 | 0.10 | 0.00 | 2.60 | 2.50 |
| Prednisolone 1 mg/kg p.o. | S.E.M. | 0.00 | 0.10 | 0.00 | 0.22 | 0.22 |

TABLE 1-continued

Disease Activity Index (DAI) score progression during Day 1 to Day 10. Significant differences from control (vehicle) group values at a given date are shown as *p < 0.05; **p < 0.01 (Kruskal-Wallis Test for non-parametric data).

| Test item | Data | DAI score | | | | |
|---|---|---|---|---|---|---|
| | | Day 6 | Day 7 | Day 8 | Day 9 | Day 10 |
| Group A Control vehicle i.v. | Mean S.E.M. | 3.10 0.31 | 4.10 0.69 | 5.90 1.26 | 8.90 1.02 | 10.90 0.62 |
| Group B hBD2 0.1 mg/kg i.v. | Mean S.E.M. | 3.20 0.20 | 1.44** 0.38 | 2.11* 0.20 | 3.89** 0.35 | 6.44** 0.85 |
| Group C hBD2 1 mg/kg i.v. | Mean S.E.M. | 2.89 0.20 | 2.22 0.43 | 3.67 0.80 | 5.22 0.83 | 6.44* 1.08 |
| Group D hBD2 10 mg/kg i.v. | Mean S.E.M. | 3.22 0.28 | 2.11 0.31 | 4.11 0.93 | 6.78 1.20 | 7.33 1.33 |
| Group E Prednisolone 1 mg/kg p.o. | Mean S.E.M. | 2.60 0.27 | 3.10 0.96 | 2.50* 0.43 | 3.80* 0.98 | 4.90** 0.91 |

Histological Evaluation

Two sections (proximal and distal) of colon were taken from each animal, processed for histological analysis (haematoxylin and eosin staining) and scored by a blind observer according to the histological scoring system described above.

Determination of TNF-α Concentration in Colonic Tissue Samples

An additional sample of colon was obtained from each animal and homogenised in PBS (100 mg tissue/ml PBS) containing 1% bovine serum albumin (BSA) and a protease inhibitor cocktail (1 ml/20 g tissue). The homogenate was then be centrifuged at 14000 rpm for 10 min and the supernatant stored at −20° C. for subsequent determination of TNF-α concentration by specific enzyme immunoassay (ELISA).

TABLE 3

Histological scores, colon weight and length, and colon TNF-α concentration. Differences in histological scores from control (vehicle) group values are shown as *p < 0.05; **p < 0.01 (Kruskal-Wallis Test for non-parametric data).

| Test item | Data | Histology Score Proximal Colon | Histology Score Distal Colon | Colon TNF-α concentration (pg/g tissue) |
|---|---|---|---|---|
| Group A Control vehicle i.v. | Mean S.E.M. | 4.20 0.25 | 4.50 0.22 | 1664 227 |
| Group B hBD2 0.1 mg/kg i.v. | Mean S.E.M. | 2.22** 0.43 | 3.67 0.47 | 1185 205 |
| Group C hBD2 1 mg/kg i.v. | Mean S.E.M. | 2.89* 0.35 | 4.13 0.35 | 1457 211 |
| Group D hBD2 10 mg/kg i.v. | Mean S.E.M. | 2.89* 0.39 | 4.78 0.15 | 1212 211 |
| Group E Prednisolone 1 mg/kg p.o. | Mean S.E.M. | 2.80* 0.51 | 3.70 0.42 | 1833 414 |

Statistical Analysis

The statistical significance of the results was evaluated using the statistics program Graphpad Instat 3. The difference between groups for disease activity index and histological score was evaluated by Kruskal-Wallis test for unpaired data plus post-test Dunn to allow for multiple comparisons. A value of p<0.05 was taken as significant.

Conclusions

The results demonstrate that hBD2 at the lowest dose tested (0.1 mg/kg i.v.) significantly reduces the increase in Disease Activity Index induced by DSS administration at day 7 (1.44±0.38 test item vs. 4.1±0.69 vehicle; p<0.01), day 8 (2.11±0.2 test item vs. 5.9±1.26 vehicle; p<0.05), day 9 (3.89±0.35 test item vs. 8.9±1.02 vehicle; p<0.01) and da (6.44±0.85 test item vs. 10.9±0.62 vehicle; p<0.05).

Treatment with the intermediate dose of hBD2 (1 mg/kg i.v.) for 10 consecutive days resulted in an apparent reduction of the disease activity index score but this was only significant on day 10 (6.44±1.08 test item vs. 10.9±0.62 vehicle; p<0.05).

Similarly to the results obtained with the Disease Activity Index on day 10, histological analysis of the proximal colons of each animal revealed a very significant reduction of histological damage score by treatment with the low dose of hBD2 (2.22±0.43 test item vs. 4.2±0.25 vehicle; p<0.01). Moreover, a significant reduction of histological injury was also observed with the intermediate and high doses of hBD2, as well as with prednisolone (2.89±0.35; 2.89±0.39 and 2.8±0.5 respectively; p<0.05). In contrast, in the distal colon—although an apparent reduction in histological injury could be observed in the animals treated with the low and intermediate dose of hBD2, as well as with prednisolone—this was not statistically significant. No reduction could be observed in the animals that were treated with the high dose of hBD2. Similarly, treatment with the low and intermediate doses of hBD2 resulted in an apparent reduction in colonic TNF-alpha levels, but this apparent reduction was not statistically significant.

The results obtained in the present study demonstrate an anti-inflammatory activity of hBD2 in the model of DSS colitis induced in the mouse after a 10-day treatment period. However, this anti-inflammatory activity appears to be more pronounced at the lower dose of hBD2 used (0.1 mg/kg/day i.v.) and is gradually lost with increasing doses up to the highest dose used in the study (10 mg/kg/day i.v.). Moreover, the anti-inflammatory effect of the lowest dose of hBD2 is comparable or even greater (e.g. histological score) than that of prednisolone at a dose of 1 mg/kg/day p.o.

Example 3

10-Day Dextran Sodium Sulphate (DSS)-induced Colitis Model in the Mouse

Example 3 was carried out essentially as described in Example 2. The differences are indicated below.

Weight

The average body weight of the animals on the day of start of the study was 19.74±0.09 g (mean±SEM).

Study Design

Animals were divided into 9 experimental groups. Each group consisted of 10 males:

Group A: Treated with control vehicle (PBS) i.v.
Group B: Treated with hBD2 (1 mg/kg i.v.)—once daily
Group C: Treated with hBD2 (0.1 mg/kg i.v.)—once daily
Group D: Treated with hBD2 (0.01 mg/kg i.v.)—once daily
Group E: Treated with hBD2 (0.001 mg/kg i.v.)—once daily
Group F: Treated with hBD2 (0.1 mg/kg i.v.+s.c.)—twice daily
Group G: Treated with hBD2 (0.1 mg/kg i.v.)—every second day
Group H: Treated with methylprednisolone (1 mg/kg p.o.)
Group J: Treated with methylprednisolone (10 mg/kg p.o.)

Animal allocation to all experimental groups was done in a randomized manner. A maximum of 5 mice were housed in each cage (as per Directive 86/609/EEC). All animals were weighed on their arrival at the laboratory and prior to the administration of the test and reference compounds.

Administration of the Test Items

The control vehicle and hBD2 were administered intravenously via the tail vein with the use of a sterile needle (25 G) in a dosing volume of 5 ml/kg body weight as a slow bolus (over a period of 15 seconds).

The animals in groups A to E received one dose daily (every 24 hours) of the corresponding test item (hBD2, prednisolone or control vehicle) for 10 consecutive days.

The animals in group F received one dose i.v. and another dose s.c. (12 hours after the i.v. dose) of the corresponding test item for 10 consecutive days.

The animals in group G received one dose every two days of the corresponding test item for 10 consecutive days.

Methylprednisolone was given orally at a dose of 1 mg/kg (group H) and 10 mg/kg (group J) in a dosing volume of 5 ml/kg body weight, once daily for 10 consecutive days.

Blood Sampling

A terminal blood sample was obtained from all animals on the last day of the study from the abdominal vena cava 2 hours after test item administration.

Blood samples were allowed to clot and then centrifuged at 3000 rpm for 10 min, and the resulting serum was frozen at −80° C. for subsequent analysis.

Results
Disease Activity Index Score

TABLE 4

Disease Activity Index (DAI) score progression during Day 1 to Day 10. Significant differences from control (vehicle) group values at a given date are shown as *p < 0.05; **p < 0.01 (Kruskal-Wallis Test for non-parametric data). Day 6 to Day 10 is shown on the next page.

| Test item | Data | Day 1 | Day 2 | Day 3 | Day 4 | Day 5 |
|---|---|---|---|---|---|---|
| Group A Control vehicle i.v. | Mean S.E.M. | 0.00 0.00 | 0.00 0.00 | 0.10 0.10 | 0.10 0.10 | 0.20 0.13 |
| Group B hBD2 1 mg/kg i.v. | Mean S.E.M. | 0.00 0.00 | 0.10 0.10 | 0.20 0.13 | 0.40 0.16 | 0.30 0.21 |
| Group C hBD2 0.1 mg/kg i.v. | Mean S.E.M. | 0.00 0.00 | 0.44 0.18 | 0.89 0.42 | 0.56 0.29 | 0.78 0.28 |
| Group D hBD2 0.01 mg/kg i.v. | Mean S.E.M. | 0.00 0.00 | 0.00 0.00 | 0.30 0.15 | 0.40 0.16 | 1.60 0.43 |
| Group E hBD2 0.001 mg/kg i.v. | Mean S.E.M. | 0.00 0.00 | 0.00 0.00 | 0.10 0.10 | 0.20 0.13 | 0.40 0.16 |
| Group F hBD2 0.1 mg/kg twice daily i.v. + s.c. | Mean S.E.M. | 0.00 0.00 | 0.30 0.21 | 0.70 0.30 | 0.70 0.34 | 0.60 0.16 |
| Group G hBD2 0.1 mg/kg i.v. every 2. day | Mean S.E.M. | 0.00 0.00 | 0.20 0.13 | 0.40 0.22 | 0.50 0.17 | 0.50 0.17 |
| Group H Prednisolone 1 mg/kg p.o. | Mean S.E.M. | 0.00 0.00 | 0.50 0.17 | 0.50 0.17 | 0.40 0.16 | 1.10 0.18 |
| Group J Prednisolone 10 mg/kg p.o. | Mean S.E.M. | 0.00 0.00 | 0.30 0.15 | 0.70 0.21 | 0.80 0.20 | 1.30 0.21 |

| Test item | Data | Day 6 | Day 7 | Day 8 | Day 9 | Day 10 |
|---|---|---|---|---|---|---|
| Group A Control vehicle i.v. | Mean S.E.M. | 6.90 1.02 | 9.67 0.33 | 11.11 0.31 | 11.67 0.17 | 11.00 0.65 |
| Group B hBD2 1 mg/kg i.v. | Mean S.E.M. | 2.30* 1.00 | 4.40* 1.03 | 6.89 1.41 | 5.00* 0.60 | 5.78* 0.70 |
| Group C hBD2 0.1 mg/kg i.v. | Mean S.E.M. | 1.56** 0.73 | 4.13* 0.83 | 5.43* 1.13 | 6.29* 1.64 | 6.86 1.14 |
| Group D hBD2 0.01 mg/kg i.v. | Mean S.E.M. | 2.70 1.08 | 6.50 1.28 | 6.20* 1.06 | 4.60*** 0.98 | 5.20** 0.87 |
| Group E hBD2 0.001 mg/kg i.v. | Mean S.E.M. | 3.40 1.32 | 7.11 1.38 | 8.56 1.06 | 5.89** 1.63 | 6.67 1.30 |
| Group F hBD2 0.1 mg/kg twice daily i.v. + s.c. | Mean S.E.M. | 0.70*** 0.30 | 3.50** 0.89 | 4.00*** 1.17 | 2.90*** 0.55 | 4.50*** 0.62 |

TABLE 4-continued

Disease Activity Index (DAI) score progression during Day 1 to Day 10.
Significant differences from control (vehicle) group values at a given
date are shown as *p < 0.05; **p < 0.01 (Kruskal-Wallis Test
for non-parametric data). Day 6 to Day 10 is shown on the next page.

| | | | | | | |
|---|---|---|---|---|---|---|
| Group G hBD2 0.1 mg/kg i.v. every 2. day | Mean S.E.M. | 2.90 1.12 | 6.50 1.11 | 8.70 1.25 | 7.50 0.93 | 6.56 0.99 |
| Group H Prednisolone 1 mg/kg p.o. | Mean S.E.M. | 3.80 0.98 | 5.90 1.16 | 6.40 0.88 | 5.60* 0.88 | 5.60* 0.65 |
| Group J Prednisolone 10 mg/kg p.o. | Mean S.E.M. | 2.00 0.30 | 3.20** 0.73 | 4.80** 0.53 | 5.20* 0.61 | 4.00*** 0.00 |

Histological Evaluation

Two sections (proximal and distal) of colon were taken from each animal, processed for histological analysis (haematoxylin and eosin staining), and scored by a blind observer according to the scoring system described above.

TABLE 5

Histological scores, colon weight and length, and colon
TNF-α concentration. Differences in histological scores
from control (vehicle) group values are shown as *p < 0.05;
**p < 0.01 (Kruskal-Wallis Test for non-parametric data).

| Test item | Data | Histology Score Proximal Colon | Histology Score Distal Colon |
|---|---|---|---|
| Group A Control vehicle i.v. | Mean S.E.M. | 2.44 0.34 | 4.67 0.17 |
| Group B hBD2 1 mg/kg i.v. | Mean S.E.M. | 1.78 0.36 | 3.56 0.38 |
| Group C hBD2 0.1 mg/kg i.v. | Mean S.E.M. | 1.71 0.18 | 3.14* 0.40 |
| Group D hBD2 0.01 mg/kg i.v. | Mean S.E.M. | 1.70 0.26 | 3.10** 0.23 |
| Group E hBD2 0.001 mg/kg i.v. | Mean S.E.M. | 1.44 0.24 | 3.56 0.18 |
| Group F hBD2 0.1 mg/kg twice daily i.v. + s.c. | Mean S.E.M. | 1.30* 0.21 | 2.90*** 0.23 |
| Group G hBD2 0.1 mg/kg i.v. every 2. day | Mean S.E.M. | 1.56 0.24 | 3.56 0.29 |
| Group H Prednisolone 1 mg/kg p.o. | Mean S.E.M. | 1.40 0.22 | 3.00*** 0.00 |
| Group J Prednisolone 10 mg/kg p.o. | Mean S.E.M. | 1.40 0.16 | 2.70*** 0.21 |

Statistical Analysis

The statistical significance of the results was evaluated using the statistics program Graphpad 5 Instat 3. The difference between groups for disease activity index and histological score was evaluated by Kruskal-Wallis test for unpaired data+post-test of Dunn for multiple comparisons. A value of p<0.05 was taken as significant. In the tables above, significant differences versus the corresponding control (vehicle) group are denoted as: *p<0.05, p<0.01, *p<0.001.

Conclusions

The aim of the present study was to determine the anti-inflammatory activity of hBD2 in an acute (10-days) model of inflammatory bowel disease (colitis) induced by oral dextran sodium sulphate (DSS, 2%) administration in the mouse.

The results obtained in the present study further demonstrate an anti-inflammatory activity of hBD2 in the model of DSS colitis induced in the mouse after a 10-day treatment period.

This anti-inflammatory activity appears to be more pronounced after administration of hBD2 twice per day (every 12 hours), both intravenously and subcutaneously, at a dose of 0.1 mg/kg. Moreover, the anti-inflammatory effect observed with this dose of hBD2 is comparable, or even greater (both on Disease Activity Index and histological score), than that of prednisolone at a dose of 1 mg/kg or 10 mg/kg given orally.

Example 4

Anti-inflammatory Activity of Human Beta Defensin 2 (hBD2)

In human PBMC cultures it was observed that treatment with hBD2 had great influence on the cytokine profile of LPS, LTA or peptidoglycan stimulated cultures. It has previously been observed that hBD2 is able to induce the proinflammatory cytokines and chemokines IL-6, IL-1β, RANTES, IP-10 and IL-8 (Niyonsaba et al. 2007, Boniotto M. et al. 2006).

Here we show that hBD2 has downregulating potential on TNF and IL-1β, two proinflammatory cytokines; and hBD2 also induces IL-10 upon induction of an inflammatory stimulus with lipopolysaccahride (LPS), lipoteichoic acid (LTA) or peptidoglycan (PGN). IL-10 is a potential anti-inflammatory cytokine and hence the resulting effect of hBD2 is anti-inflammatory. This has been observed for human PBMC, a monocytic cell line and a dendritoid cell line.

hBD2 was prepared as described in Example 1.

Isolation and Stimulation of PBMC.

Peripheral blood was drawn from healthy volunteers (with approval from the relevant ethical committee in Denmark). Heparinized blood was diluted 1/1 v/v with RPMI and were subjected to Ficoll density centrifugation within 2 h of drawing. Plasma was collected from the top from individual donors and was kept on ice until it was used at 2% in the culture medium (autologous culture medium). Isolated PBMC were resuspended in autologous culture medium and seeded in 96-well culture plates with 255.000 cells per well in a total of 200 μl. PBMC from the same donor were stimulated with 100, 10 or 1 μg/ml of hBD2 either alone or together with LPS at 0.6 ng/ml or 20 ng/ml (E. coli, O111 :B4, Sigma L4391), Lipoteichoic acid (LTA) at 1.25 μg/ml (from B. subtilis, Sigma L3265) or peptidoglycan (PGN) at 40 μg/ml (from S. aureus, Sigma 77140). The concentrations used for stimulation were optimized on 3 different donors in initial experiments, for LPS two different concentrations were used to be sure to be on a cytokine level that is possible to modulate. In some experiments PBMC were treated with Dexamethason and Indomethacin alone and together with LPS or LTA as a control on downregulation of inflammatory cytokines. The supernatants were collected after incubation at 37° C. for 24 hours, and stored at −80° C. until cytokine measurement. Viability was measured by Alamar Blue (Biosource, DALL 1100) in all experiments and in some cases also by MTS (Promega) according to manufacturer's instruction and was in some experiments also judged by counting of the cells by a Nucleocounter.

Culture and Stimulation of MUTZ-3

The human myeloid leukaemia-derived cell line MUTZ-3 (DSMZ, Braunschweig, Germany) was maintained in a-MEM (Sigma M4526), supplemented with 20% [volume/volume (v/v)] fetal bovine serum (Sigma F6178) and 40 ng/ml rhGM-CSF (R&D Systems 215-GM-050). These progenitor cells is in the following denoted monocyte cell line and these monocytes were stimulated with 100, 10 or 1 µg/ml of hBD2 either alone or together with LPS or LTA.

Dendritic Cell Differentiation

To generate a dendritoid cell line, the human myeloid leukaemia cell lines MUTZ-3 ($1\times10^5$ cells/ml) was differentiated for 7 days in the presence of rhGM-CSF (150 ng/ml) and rhIL-4 (50 ng/ml) into immature DCs. Medium was exchanged every 2-3 days. The differentiated cell line was further stimulated with either LPS or LTA with and without hBD2 to explore the effect of hBD2 on dendritic cells.

Cytokine Measurements.

Cytokine production in supernatants was measured by flow cytometry with a human inflammation cytometric bead array (CBA) according to manufacturer's instructions (BD) on a FACSarray flow cytometer. The following cytokines were measured: IL-8, IL-1β, IL-10, TNF, IL-12 p70, IL-6. In some experiments, cytokines were measured by ELISA kits from R&D systems (IL-10, TNF-α, IL-1β) according to the manufacturer' instruction.

Data Analysis

All experiments were performed at least twice, with representative results shown. The data presented are expressed as mean plus/minus standard deviation (SD). Statistical significance was determined by 2-way ANOVA with the variables being treatment (hBD2, dexamethazone, etc.) and stimulation (LPS, LTA, peptidoglycan, ect.) followed by Bonferroni post-test as reported in the table legends. Differences were considered significant for $p<0.05$.

Results

The effect of hBD2 was tested on human PBMC treated with and without LPS and LTA (Tables 6, 7 and 8). Treatment with hBD2 gave a significant downregulation of TNF in stimulated cultures for all three tested concentrations (Table 6), the downregulation is dose-dependent for LPS at 0.6 ng/ml and for LTA. For IL-1β the downregualtion was observed mostly at the highest doses (Table 7). Interestingly, IL-10 was significantly and dose-dependently upregulated (Table 8). Downregulation of proinflammatory cytokines and induction of anti-inflammatory cytokines shows a very strong anti-inflammatory potential of hBD2. Viability was measured by two different assays, in order to exclude that the anti-inflammatory effects of hBD2 is due to cytotoxic effects. In Tables 9 and 10 it can be seen that hBD2 have no cytotoxic effect on the cells, the observed effects are stimulatory effects due to stimulation with LPS or LTA that leads to proliferation of the cells. Therefore hBD2 has no cytotoxic effect on these cells.

In Tables 11, 12 and 13, supernatants from another donor were analysed for cytokines by ELISA instead of by a cytometric bead array by flowcytometry and here the same were observed, although the sensitivity of the assay is lower and the detection limit much higher and therefore the effects were not as significant.

In order to test yet another Toll-like receptor ligand, the effect of hBD2 on peptidoglycan stimulated PBMC was investigated (Tables 14 and 15). The same was observed: TNF is dose-dependently downregulated and IL-10 is dose-dependently induced.

As a positive control on downregulation of TNF, two anti-inflammatory compounds, dexamethasone and Indomethacin, were tested in the assay. The concentrations are selected so the compounds are not toxic and achievable concentration due to solubility in medium. Indomethacin only inhibited TNF (Table 16) after stimulation with LTA, whereas dexamethasone effectively downregulated TNF production, the same was observed for IL-1β (Table 18). Indomethacin is a COX-1 and COX-2 inhibitor and is a nonsteroidal anti-inflammatory drug (NSAID) used to treat mild to moderate pain and help relieve symptoms of arthritis and dexamethasone is a synthetic glucocorticoid used primarily in the treatment of inflammatory disorders and it has very potent downregualting effect on proinflammatory cytokines (Rowland et al. 1998) at very low doses, which we also observe for TNF-α and IL-1β. hBD2 is as effective as or better than these two anti-inflammatory compounds.

In Tables 19 and 20, the effect of hBD2 on downregulating TNF in a monocyt cell line and on dendritic cells are shown, the same is observed as was for PBMC. IL-10 was also induced for dendritic cells stimulated with hBD2 and LPS or hBD2 and LTA (results not shown).

In order to exclude that binding of hBD2 to LPS or LTA causes the downregulation of TNF and IL-1β, the effect of hBD2 on stimulation of PBMC with a synthetic ligand (Pam3CSK4 (TLR2-TLR1 ligand), InvivoGen tlrt-pms) was tested. hBD2 was able to downregulate TNF after stimulation with this ligand as well, indicating that neutralization of LPS or LTA is not responsible for the observed effect (results not shown). Moreover, stimulation of dendritic cells with a cytokine cocktail containing TNF-α and IL-α together with hBD2 had downregulating effect on IL-1β and IL-8 and IL-6 compared to stimulation with a cytokine cocktail alone. Obviously no effect on TNF could be analyzed, due to stimulation with TNF-α (results not shown).

TABLE 6

TNF production from human peripheral blood mononuclear cells (PBMC) after treatment with LPS or LTA with and without hBD2, all samples tested on the same donor, representative experiment out of 5 donors. TNF measured by Cytometric Bead Array (CBA) on a FACSarray, \*\*\*p < 0.001 compared to respective control (bold), analysed by 2-way ANOVA (N = app. 200 for each data set).

| TNF, pg/ml (SD) | Control | hBD2 100 µg/ml | hBD2 10 µg/ml | hBD2 1 µg/ml |
|---|---|---|---|---|
| Medium | 7.3 (5.9) | 2.9 (5.1) | 2.6 (6.6) | 4.2 (10.7) |
| LPS 0.6 ng/ml | 1708.6 (428.3) | 634.2 (226.1)\*\*\* | 1076.4 (278.0)\*\*\* | 944.8 (326.6)\*\*\* |
| LPS 20 ng/ml | 2572.1 (581.1) | 1733.9 (461.3)\*\*\* | 1306.6 (375.0)\*\*\* | 1526.9 (444.2)\*\*\* |
| LTA 1.25 µg/ml | 1097.4 (293.8) | 375.2 (114.2)\*\*\* | 494.7 (158.1)\*\*\* | 711.5 (282.5)\*\*\* |

TABLE 7

IL-1β production from human peripheral blood mononuclear cells (PBMC) after treatment with LPS or LTA with and without hBD2, all samples tested on the same donor, representative experiment out of 5 donors. IL-1β measured by Cytometric bead array (CBA) on a FACSarray, ***$p < 0.001$ analysed by 2-way ANOVA (N = app. 200 for each data set).

| IL-1β, pg/ml (SD) | Control | hBD2 100 µg/ml | hBD2 10 µg/ml | hBD2 1 µg/ml |
|---|---|---|---|---|
| Medium | 4.2 (4.7) | 5.3 (7.1) | 3.8 (5.8) | 4.1 (51.0) |
| LPS 0.6 ng/ml | 1734.3 (347.0) | 811.0 (454.4)*** | 1949.8 (396.4)*** | 1436.2 (429.7)*** |
| LPS 20 ng/ml | 2629.5 (533.7) | 1502.1 (407.5)*** | 2273.9 (486.5)*** | 1889.3 (504.8)*** |
| LTA 1.25 µg/ml | 748.5 (172.4) | 538.3 (137.3)*** | 935.3 (238.0)*** | 986.7 (738.7)*** |

TABLE 8

IL-10 production from human peripheral blood mononuclear cells (PBMC) after treatment with LPS or LTA with and without hBD2, all samples tested on the same donor, representative experiment out of 5 donors. IL-10 measured by Cytometric bead array (CBA) on a FACSarray, *$p < 0.001$, $p < 0.01$, *$p < 0.5$ analysed by 2-way ANOVA (N = app. 200 for each data set).

| IL-10, pg/ml (SD) | Control | hBD2 100 µg/ml | hBD2 10 µg/ml | hBD2 1 µg/ml |
|---|---|---|---|---|
| Medium | 2.09 (8.65) | 2.9 (4.6) | 1.6 (4.1) | 2.09 (4.3) |
| LPS 0.6 ng/ml | 63.15 (302.5) | 232.7 (61.5)*** | 325.7 (88.2)*** | 97.2 (31.1)* |
| LPS 20 ng/ml | 70.4 (22.8) | 383.3 (133.6)*** | 355.8 (99.5)*** | 111.3 (38.8)** |
| LTA 1.25 µg/ml | 14.0 (226.1) | 175.6 (57.0)*** | 136.6 (44.7)*** | 39.9 (16.9) |

TABLE 9

PBMC viability after 24 h of stimulation measured by a MTS assay. Values having a different subscript letter in rows are significantly different tested by 2-way ANOVA followed by Bonferroni post-test.

| Viability, MTS (Abs 490 nm (SD)) | Control | hBD2 100 µg/ml | hBD2 10 µg/ml | hBD2 1 µg/ml |
|---|---|---|---|---|
| Medium | 1.4 (0.2) | 1.2 (0.05)$^a$ | 1.5 (0.2)$^a$ | 1.3 (0.2) |
| LPS 0.6 ng/ml | 1.6 (0.02) | 1.6 (0.1)$^{ab}$ | 2.0 (0.2)$^b$ | 1.5 (0.2) |
| LPS 20 ng/ml | 1.5 (0.1) | 1.9 (0.2)$^b$ | 1.8 (0.3)$^{ab}$ | 1.6 (0.3) |

TABLE 10

PBMC viability measured by Alamar Blue, one representative experiment out of 5 from 5 different donors. Values having a different superscript letter in rows and values having a different superscript number in columns are significantly different tested by 2-way ANOVA followed by Bonferroni post-test.

| Viability, Alamar Blue (RFU (SD)) | Control | hBD2 100 µg/ml | hBD2 10 µg/ml | hBD2 1 µg/ml |
|---|---|---|---|---|
| Medium | 4097130 (166631) | 3950053 (34466)$^a$ | 3683369 (355296)$^a$ | 4064143 (104634) |
| LPS 0.6 ng/ml | 4279424 (336188) | 4831188 (67646)$^b$ | 4664362 (147776)$^b$ | 4230588 (139745) |
| LPS 20 ng/ml | 4604671 (125840) | 4765256 (41383)$^b$ | 4623818 (56643)$^b$ | 4561739 (138852) |
| LTA 1.25 µg/ml | 4018914 (632833)$^1$ | 4664185 (154023)$^{b,2}$ | 4677870 (10199)$^{b,2}$ | 4148294 (182730)$^{12}$ |

TABLE 11

TNF-alfa secretion from PBMC after stimulation with hBD2, LTA, LPS or combinations hereof. TNF-alfa measured by ELISA, nd: not detectable, detection limit in assay 0.01 ng/ml, *$p < 0.05$ compared to respective control, **$p < 0.01$ compared to respective control

| TNF-α, ng/ml (SD) | Control | hBD2 100 µg/ml | hBD2 10 µg/ml | hBD2 1 µg/ml |
|---|---|---|---|---|
| Medium | nd | nd | nd | nd |
| LPS 0.6 ng/ml | 0.99 (0.27) | 0.41 (0.03)** | 0.59 (0.08)* | 0.70 (0.18) |
| LPS 20 ng/ml | 1.44 (0.31) | 0.53 (0.01)** | 0.49 (0.05)** | 1.18 (0.42) |
| LTA 1.25 µg/ml | 0.90 (0.32) | 0.21 (0.05)* | 0.27 (0.04)* | 0.65 (0.29) |

TABLE 12

IL-10 secretion from PBMC after stimulation with hBD2, LTA, LPS or combinations hereof, TNF-alfa measured by ELISA, nd: not detectable, detection limit in assay 0.03 ng/ml

| IL-10, ng/ml (SD) | Control | hBD2 100 µg/ml | hBD2 10 µg/ml | hBD2 1 µg/ml |
|---|---|---|---|---|
| Medium | nd | nd | nd | nd |
| LPS 0.6 ng/ml | nd | 0.14 (0.04) | 0.04 (0.0) | nd |
| LPS 20 ng/ml | nd | 0.46 (0.04) | 0.34 (0.04) | nd |
| LTA 1.25 µg/ml | nd | nd | nd | nd |

TABLE 13

IL-1β secretion from PBMC after stimulation with hBD2, LTA, LPS or combinations hereof, TNF-alfa measured by ELISA, nd: not detectable, detection limit in assay 0.016 ng/ml, **$p < 0.01$ compared to respective control

| IL-10, ng/ml (SD) | Control | hBD2 100 µg/ml | hBD2 10 µg/ml | hBD2 1 µg/ml |
|---|---|---|---|---|
| Medium | nd | nd | nd | nd |
| LPS | 0.318 | 0.275 | 0.268 | 0.237 |

TABLE 13-continued

IL-1β secretion from PBMC after stimulation with hBD2, LTA, LPS or combinations hereof, TNF-alfa measured by ELISA, nd: not detectable, detection limit in assay 0.016 ng/ml, **p < 0.01 compared to respective control

| IL-10, ng/ml (SD) | Control | hBD2 100 μg/ml | hBD2 10 μg/ml | hBD2 1 μg/ml |
|---|---|---|---|---|
| 0.6 ng/ml | (0.087) | (0.015) | (0.039) | (0.007) |
| LPS | 0.920 | 0.395 | 0.354 | 0.638 |
| 20 ng/ml | (0.267) | (0.033)** | (0.013)** | (0.159) |
| LTA | 0.291 | 0.281 | 0.193 | 0.224 |
| 1.25 μg/ml | (0.092) | (0.059) | (0.019) | (0.030) |

TABLE 14

TNF production from human peripheral blood mononuclear cells (PBMC) after treatment with PGN, with and without hBD2; all samples tested on the same donor. TNF measured by Cytometric Bead Array (CBA) on a FACSarray, ***p < 0.001 compared to respective control, analysed by 2-way ANOVA (N = app. 200 for each data set).

| TNF, pg/ml (SD) | Control | hBD2 100 μg/ml | hBD2 10 μg/ml | hBD2 1 μg/ml |
|---|---|---|---|---|
| Medium | 0.0 | 3.6 | 3.7 | 3.4 |
|  | (4.0) | (5.3) | (6.2) | (5.2) |
| PGN | 1099.1 | 274.9 | 362.0 | 809.9 |
| 40 μg/ml | (251.6) | (71.6)*** | (97.7)*** | (246.7)*** |

TABLE 15

IL-10 production from human peripheral blood mononuclear cells (PBMC) after treatment with PGN, with and without hBD2; all samples tested on the same donor. TNF measured by Cytometric Bead Array (CBA) on a FACSarray, ***p < 0.001 compared to respective control, analysed by 2-way ANOVA (N = app. 200 for each data set).

| IL-10, pg/ml (SD) | Control | hBD2 100 μg/ml | hBD2 10 μg/ml | hBD2 1 μg/ml |
|---|---|---|---|---|
| Medium | 0.0 | 3.0 | 3.6 | 3.0 |
|  | (4.1) | (9.6) | (13.1) | (4.8) |
| PGN | 381.3 | 1054.2 | 523.4 | 337.8 |
| 40 μg/ml | (92.3) | (179.3)*** | (111.5)*** | (89.1) |

TABLE 16

TNF production from human peripheral blood mononuclear cells (PBMC) after treatment with LPS or LTA, with and without hBD2 or two different controls for inhibition of TNF (Dexamethasone and Indomethacin); all samples tested on the same donor. TNF measured by Cytometric Bead Array (CBA) on a FACSarray, values underlined are significantly reduced compared to respective control (bold), analysed by 2-way ANOVA (N = app. 200 for each data set).

| TNF, ng/ml (SD) | Medium | LPS 0.6 ng/ml | LPS 20 ng/ml | LTA 1.25 μg/ml |
|---|---|---|---|---|
| Control | 0.0 | 1.43 | 2.84 | 6.72 |
|  | (0.0) | (0.05) | (0.07) | (0.14) |
| Dexamethason | 0.0 | <u>0.038</u> | <u>1.69</u> | <u>1.75</u> |
| 35 ng/ml | (0.0) | (0.004) | (0.05) | (0.05) |
| Dexamethason | 0.0 | <u>0.30</u> | <u>0.91</u> | <u>2.05</u> |
| 3.5 ng/ml | (0.0) | (0.01) | (0.03) | (0.06) |
| Dexamethason | 0.0 | <u>0.61</u> | 6.04 | <u>4.73</u> |
| 0.35 ng/ml | (0.0) | (0.02) | (0.14) | (0.10) |
| Indomethacin | 0.0 | 1.71 | 2.70 | <u>5.80</u> |
| 7.2 ug/ml | (0.0) | (0.07) | (0.07) | (0.13) |
| Indomethacin | 0.0 | 1.56 | 7.54 | <u>5.50</u> |

TABLE 16-continued

TNF production from human peripheral blood mononuclear cells (PBMC) after treatment with LPS or LTA, with and without hBD2 or two different controls for inhibition of TNF (Dexamethasone and Indomethacin); all samples tested on the same donor. TNF measured by Cytometric Bead Array (CBA) on a FACSarray, values underlined are significantly reduced compared to respective control (bold), analysed by 2-way ANOVA (N = app. 200 for each data set).

| TNF, ng/ml (SD) | Medium | LPS 0.6 ng/ml | LPS 20 ng/ml | LTA 1.25 μg/ml |
|---|---|---|---|---|
| 0.72 ug/ml | (0.0) | (0.04) | (0.17) | (0.13) |
| hBD2 | 0.0 | <u>0.003</u> | <u>0.000</u> | <u>0.11</u> |
| 1000 μg/ml | (0.0) | (0.002) | (0.002) | (0.01) |
| hBD2 | 0.0 | <u>0.000</u> | <u>0.038</u> | <u>1.15</u> |
| 100 μg/ml | (0.0) | (0.002) | (0.003) | (0.04) |
| hBD2 | 0.0 | <u>0.20</u> | <u>0.35</u> | <u>2.33</u> |
| 10 μg/ml | (0.0) | (0.01) | (0.01) | (0.06) |
| hBD2 | 0.0 | <u>0.17</u> | 6.24 | <u>3.90</u> |
| 1 μg/ml | (0.0) | (0.01) | (0.14) | (0.10) |

TABLE 17

IL-10 production from human peripheral blood mononuclear cells (PBMC) after treatment with LPS or LTA, with and without hBD2 or two different controls for antiinflammatory effects (Dexamethasone and Indomethacin); all samples tested on the same donor. IL-10 measured by Cytometric Bead Array (CBA) on a FACSarray, values underlined are significantly increased compared to respective control (bold), analysed by 2-way ANOVA (N = app. 200 for each data set).

| IL-10, pg/ml (SD) | Medium | LPS 0.6 ng/ml | LPS 20 ng/ml | LTA 1.25 μg/ml |
|---|---|---|---|---|
| Control | 0.0 | 53.9 | 123.4 | 170.1 |
|  | (218.8) | (3.1) | (4.6) | (5.5) |
| Dexamethason | 0.0 | 100.4 | 152.5 | 175.2 |
| 35 ng/ml | (1.4) | (3.8) | (5.2) | (6.6) |
| Dexamethason | 2.7 | 64.6 | 122.8 | 112.5 |
| 3.5 ng/ml | (1.9) | (3.3) | (4.7) | (3.9) |
| Dexamethason | 3.9 | 46.8 | 197.1 | 126.6 |
| 0.35 ng/ml | (1.9) | (2.8) | (7.2) | (4.7) |
| Indomethacin | 0.0 | 45.7 | 77.9 | 90.4 |
| 7.2 ug/ml | (1.5) | (2.5) | (3.6) | (4.9) |
| Indomethacin | 0.0 | 37.3 | 108.0 | 84.9 |
| 0.72 ug/ml | (1.4) | (19.6) | (4.4) | (3.5) |
| hBD2 | 0.0 | 30.8 | 50.5 | <u>465.2</u> |
| 1000 μg/ml | (1.6) | (2.6) | (3.2) | (16.3) |
| hBD2 | 0.0 | <u>173.5</u> | <u>885.2</u> | <u>766.0</u> |
| 100 μg/ml | (4.9) | (5.7) | (22.2) | (21.7) |
| hBD2 | 3.9 | <u>165.1</u> | <u>497.5</u> | <u>355.8</u> |
| 10 μg/ml | (1.7) | (5.6) | (13.5) | (9.4) |
| hBD2 | 0.0 | 42.7 | <u>207.0</u> | 142.1 |
| 1 μg/ml | (1.9) | (2.8) | (6.9) | (4.9) |

TABLE 18

IL-1β production from human peripheral blood mononuclear cells (PBMC) after treatment with LPS or LTA, with and without hBD2 or two different controls for antiinflammatory effects (Dexamethasone and Indomethacin); all samples tested on the same donor. IL-1β measured by Cytometric Bead Array (CBA) on a FACSarray, values underlined are significantly reduced compared to respective control (bold), analysed by 2-way ANOVA (N = app. 200 for each data set).

| IL-1β, ng/ml (SD) | Medium | LPS 0.6 ng/ml | LPS 20 ng/ml | LTA 1.25 μg/ml |
|---|---|---|---|---|
| Control | 0.00 | 3.96 | 6.58 | 11.47 |
|  | (0.06) | (0.18) | (0.23) | (0.38) |
| Dexamethason | 0.00 | <u>1.00</u> | <u>2.32</u> | <u>3.98</u> |
| 35 ng/ml | (0.00) | (0.03) | (0.07) | (0.14) |
| Dexamethason | 0.00 | <u>1.90</u> | <u>3.58</u> | <u>5.22</u> |

TABLE 18-continued

IL-1β production from human peripheral blood mononuclear cells
(PBMC) after treatment with LPS or LTA, with and without hBD2 or
two different controls for antiinflammatory effects (Dexamethasone
and Indomethacin); all samples tested on the same donor. IL-1β
measured by Cytometric Bead Array (CBA) on a FACSarray, values
underlined are significantly reduced compared to respective control
(bold), analysed by 2-way ANOVA (N = app. 200 for each data set).

| IL-1β, ng/ml (SD) | Medium | LPS 0.6 ng/ml | LPS 20 ng/ml | LTA 1.25 μg/ml |
|---|---|---|---|---|
| 3.5 ng/ml | (0.00) | (0.06) | (0.12) | (0.19) |
| Dexamethason 0.35 ng/ml | 0.01 (0.00) | 2.9 (0.09) | 5.56 (0.18) | 7.91 (0.28) |
| Indomethacin 7.2 μg/ml | 0.04 (0.00) | 4.1 (0.13) | 6.12 (0.23) | 8.91 (0.30) |
| Indomethacin 0.72 ug/ml | 0.01 (0.00) | 3.1 (0.18) | 6.46 (0.22) | 7.53 (0.31) |
| hBD2 1000 μg/ml | 0.01 (0.00) | 0.53 (0.02) | 1.19 (0.08) | 4.43 (0.14) |
| hBD2 100 μg/ml | 0.00 (0.00) | 0.38 (0.01) | 1.67 (0.05) | 9.12 (0.32) |
| hBD2 10 μg/ml | 0.06 (0.00) | 1.13 (0.04) | 3.58 (0.12) | 11.0 (0.37) |
| hBD2 1 μg/ml | 0.01 (0.00) | 1.83 (0.06) | 4.91 (0.19) | 8.87 (0.29) |

TABLE 19

TNF production in supernatant from a human monocyte cell line
(MUTZ-3) after treatment with LPS or LTA, with and without hBD2.
TNF measured by Cytometric Bead Array (CBA) on a FACSarray,
*p < 0.05 compared to respective control, **p < 0.01 compared to
respective control, analysed by 2-way ANOVA (N = app. 200 for
each data set).

| TNF, pg/ml (SD) | Control | hBD2 100 μg/ml | hBD2 10 μg/ml | hBD2 1 μg/ml |
|---|---|---|---|---|
| Medium | 0.00 (5.56) | 0.00 (5.47) | 2.60 (7.17) | 2.21 (7.88) |
| LPS 1.5 μg/ml | 6.38 (9.28) | 3.93 (6.63)* | 3.93 (6.93)* | 6.61 (9.17) |
| LTA 1.5 μg/ml | 5.28 (9.75) | 2.64 (29.19)* | 3.76 (7.72) | 1.75 (6.96)** |

TABLE 20

TNF production in supernatants from immature dendritic cells stimulated
with LPS or LTA (to generate mature DC), with and without hBD2. TNF
measured by Cytometric Bead Array (CBA) on a FACSarray,
*significantly reduced p < 0.05 compared to respective control,
***significantly reduced p < 0.01 compared to respective control,
analysed by 2-way ANOVA (N = app. 200 for each data set).

| TNF, pg/ml (SD) | Control | hBD2 100 μg/ml | hBD2 10 μg/ml | hBD2 1 μg/ml |
|---|---|---|---|---|
| Medium | 0.00 (1.74) | 0.00 (1.83) | 1.89 (2.15) | 4.64 (10.26) |
| LPS 1.5 μg/ml | 23.73 (3.28) | 7.66 (2.51)*** | 13.8 (2.33)*** | 18.04 (2.89)*** |
| LTA 1.5 μg/ml | 3.78 (2.26) | 5.22 (2.25) | 2.76 (2.27)* | 0.00 (1.98)*** |

Example 5

Anti-inflammatory Activity of hBD1, hBD2, hBD3, and a hBD4 Variant

Example 5 was carried out essentially as described in Example 4. The compound rhBD2, as shown in the tables below, is recombinant hBD2, which is identical to hBD2 as used in Example 4.

The compounds hBD1, hBD2, hBD3 and hBD4 variant, as shown in the tables below, were prepared using chemical synthesis, and obtained from Peptide Institute Inc.

The amino acid sequence of recombinant hBD2 (rhBD2) is identical to the amino acid sequence of hBD2 prepared by chemical synthesis.

The hBD4 variant shown in the tables below consists of amino acids 3-39 of hBD4, and the amino acid sequence is shown as SEQ ID NO:5.

In each table, all samples were tested on the same donor. SD means standard deviation.

Results

TABLE 21

TNF production from human peripheral blood mononuclear cells (PBMC)
after treatment with LPS with and without human beta defensins,
dexamethasone or Infliximab. TNF measured by Cytometric Bead Array
(CBA) on a FACSarray, *p < 0.05, **p < 0.01,
***p < 0.001 analyzed by 2-way ANOVA and compared to non-treated
cells by Bonferroni posttests.

| Test compound | Medium TNF pg/ml (SD) | Medium % of control | LPS 20 ng/ml TNF pg/ml (SD) | LPS 20 ng/ml % of control | LPS 0.6 ng/ml TNF pg/ml (SD) | LPS 0.6 ng/ml % of control |
|---|---|---|---|---|---|---|
| Medium (non-treated) | 1 (1) | 100% | 2164 (632) | 100% | 728 (156) | 100% |
| rhBD2 40 μg/ml | 0 (0) | — | 167 (17)*** | 8% | 74 (5)*** | 10% |
| rhBD2 10 μg/ml | 0 (0) | — | 260 (29)*** | 12% | 125 (20)** | 17% |
| rhBD2 1 μg/ml | 1 (0) | — | 918 (373)*** | 42% | 196 (104)** | 27% |
| hBD1 40 μg/ml | 0 (0) | — | 999 (116)*** | 46% | 91 (8)** | 13% |
| hBD1 10 μg/ml | 0 (1) | — | 1311 (417)*** | 61% | 203 (20)** | 28% |
| hBD1 | 1 | — | 1395 | 64% | 474 | 65% |

TABLE 21-continued

TNF production from human peripheral blood mononuclear cells (PBMC) after treatment with LPS with and without human beta defensins, dexamethasone or Infliximab. TNF measured by Cytometric Bead Array (CBA) on a FACSarray, $*p < 0.05$, $p < 0.01$, $*p < 0.001$ analyzed by 2-way ANOVA and compared to non-treated cells by Bonferroni posttests.

| Test compound | Medium TNF pg/ml (SD) | % of control | LPS 20 ng/ml TNF pg/ml (SD) | % of control | LPS 0.6 ng/ml TNF pg/ml (SD) | % of control |
|---|---|---|---|---|---|---|
| 1 µg/ml | (1) | | (201)*** | | (187) | |
| hBD2 40 µg/ml | 0 (0) | — | 52 (71)*** | 2% | 176 (103)** | 24% |
| hBD2 10 µg/ml | 0 (0) | — | 132 (179)*** | 6% | 304 (108)* | 42% |
| hBD2 1 µg/ml | 0 (0) | — | 411 (581)*** | 19% | 242 (30)* | 33% |
| HBD-3 1 µg/ml | 0 (0) | — | 451 (24)*** | 21% | 528 (98) | 73% |
| hBD4 variant 10 µg/ml | 0 (0) | — | 139 (6)*** | 6% | 211 (22)** | 29% |
| hBD4 variant 1 µg/ml | 0 (0) | — | 778 (27)*** | 36% | 468 (59) | 64% |
| Dexamethasone | 0 (0) | — | 635 (163)*** | 29% | 47 (8)*** | 6% |
| Infliximab | 0 (0) | — | 0 (0)*** | 0% | 0 (0)*** | 0% |

TABLE 22

IL-10 production from human peripheral blood mononuclear cells (PBMC) after treatment with LPS with and without human beta defensins, dexamethasone or Infliximab. IL-10 measured by Cytometric Bead Array (CBA) on a FACSarray, $*p < 0.05$, $p < 0.01$, $*p < 0.001$ analyzed by 2-way ANOVA and compared to non-treated cells by Bonferroni posttests.

| Test compound | Medium IL-10 pg/ml (SD) | % of control | LPS 20 ng/ml IL-10 pg/ml (SD) | % of control | LPS 0.6 ng/ml IL-10 pg/ml (SD) | % of control |
|---|---|---|---|---|---|---|
| Medium (non-treated) | 0 (0) | 100% | 111 (3) | 100% | 66 (5) | 100% |
| rhBD2 40 µg/ml | 0 (0) | — | 281 (9)*** | 252% | 108 (4)* | 162% |
| rhBD2 10 µg/ml | 0 (0) | — | 243 (38)*** | 218% | 103 (14)* | 155% |
| rhBD2 1 µg/ml | 0 (0) | — | 126 (14) | 113% | 72 (9) | 108% |
| hBD1 40 µg/ml | 0 (0) | — | 113 (5) | 102% | 69 (4) | 104% |
| hBD1 10 µg/ml | 0 (0) | — | 100 (1) | 90% | 76 (13) | 114% |
| hBD1 1 µg/ml | 0 (0) | — | 95 (17) | 85% | 71 (6) | 108% |
| hBD2 40 µg/ml | 0 (0) | — | 323 (0)*** | 290% | 131 (13)*** | 197% |
| hBD2 10 µg/ml | 0 (0) | — | 240 (0)*** | 215% | 86 (6) | 130% |
| hBD2 1 µg/ml | 0 (0) | — | 123 (0) | 110% | 53 (5) | 80% |
| hBD3 1 µg/ml | 0 (0) | — | 152 (72)* | 137% | 71 (2) | 107% |
| hBD4 variant 10 µg/ml | 0 (0) | — | 187 (9)*** | 168% | 92 (17) | 139% |
| hBD4 variant 1 µg/ml | 0 (0) | — | 175 (8)*** | 157% | 90 (14) | 136% |

TABLE 22-continued

IL-10 production from human peripheral blood mononuclear cells (PBMC) after treatment with LPS with and without human beta defensins, dexamethasone or Infliximab. IL-10 measured by Cytometric Bead Array (CBA) on a FACSarray, *p < 0.05, p < 0.01, *p < 0.001 analyzed by 2-way ANOVA and compared to non-treated cells by Bonferroni posttests.

| Test compound | Medium IL-10 pg/ml (SD) | % of control | LPS 20 ng/ml IL-10 pg/ml (SD) | % of control | LPS 0.6 ng/ml IL-10 pg/ml (SD) | % of control |
|---|---|---|---|---|---|---|
| Dexamethasone | 0 (0) | — | 75 (6)* | 67% | 47 (3) | 70% |
| Infliximab | 0 (0) | — | 63 (7)** | 56% | 46 (9) | 69% |

TABLE 23

IL-1β production from human peripheral blood mononuclear cells (PBMC) after treatment with LPS with and without human beta defensins, dexamethasone or Infliximab. IL-1β measured by Cytometric Bead Array (CBA) on a FACSarray, ***p < 0.001 analyzed by 2-way ANOVA and compared to non-treated cells by Bonferroni posttests.

| Test compound | Medium IL-1β pg/ml (SD) | % of control | LPS 20 ng/ml IL-1β pg/ml (SD) | % of control | LPS 0.6 ng/ml IL-1β pg/ml (SD) | % of control |
|---|---|---|---|---|---|---|
| Medium (non-treated) | 0 (0) | 100% | 2544 (226) | 100% | 741 (93) | 100% |
| rhBD2 40 µg/ml | 0 (0) | — | 395 (25)*** | 16% | 124 (11)*** | 17% |
| rhBD2 10 µg/ml | 0 (0) | — | 624 (37)*** | 25% | 214 (7)*** | 29% |
| rhBD2 1 µg/ml | 0 (0) | — | 1480 (154)*** | 58% | 284 (15)*** | 38% |
| hBD1 40 µg/ml | 0 (0) | — | 1599 (14)*** | 63% | 302 (3)*** | 41% |
| hBD1 10 µg/ml | 0 (0) | — | 1913 (53)*** | 75% | 401 (17)*** | 54% |
| hBD1 1 µg/ml | 0 (0) | — | 2087 (157)*** | 82% | 512 (45)** | 69% |
| hBD2 40 µg/ml | 1 (1) | — | 316 (0)*** | 12% | 159 (2)*** | 21% |
| hBD2 10 µg/ml | 0 (0) | — | 589 (0)*** | 23% | 238 (124)*** | 32% |
| hBD2 1 µg/ml | 0 (0) | — | 1569 (0)*** | 62% | 312 (28)*** | 42% |
| hBD3 1 µg/ml | 0 (0) | — | 568 (126)*** | 22% | 331 (23)*** | 45% |
| hBD4 variant 10 µg/ml | 0 (0) | — | 463 (40)*** | 18% | 163 (5)*** | 22% |
| hBD4 variant 1 µg/ml | 0 (0) | — | 1004 (24)*** | 40% | 286 (11)*** | 39% |
| Dexamethasone | 0 (0) | — | 1120 (220)*** | 44% | 104 (8)*** | 14% |
| Infliximab | 0 (0) | — | 2704 (0) | 106% | 636 (81) | 86% |

The effects of hBD1, hBD2, hBD3 and a hBD4 variant were tested on human PBMC treated with and without LPS (Tables 21, 22 and 23). For comparison, rhBD2 was included in each setup.

TNF was downregulated for all defensins. The reduction in IL-1β secretion was comparable to TNF, although not as pronounced as TNF. Secretion of IL-10 was significantly and dose-dependently enhanced for hBD2 and the hBD4 variant. hBD3 was also tested at 10 µg/ml and 40 µg/ml and the hBD4 variant was also tested at 40 µg/ml; however, since both molecules were toxic to the cells at the these concentrations, it was not possible to discriminate between toxic and anti-inflammatory effects.

As a positive control on downregulation of TNF, two anti-inflammatory compounds, Dexamethasone and Infliximab, were included in the setup.

Conclusion

All the tested human beta defensins showed anti-inflammatory potential.

Example 6

Reduction of IL-23 from Human Monocyte-derived Dendritic Cells and Human PBMCs Example 6 was carried out essentially as described in Example 4 for human PBMCs; however, the readout was IL-23 instead of TNF, IL-1 β and IL-10. Moreover, the effect of rhBD2 on human monocyte-derived dendritic cells was also investigated.

Generation of Monocyte-Derived Dendritic Cells (DCs)

The DCs were prepared according to a modified protocol originally described by Romani et al. Briefly, peripheral blood mononuclear cells (PBMCs) were purified from buffy coats of healthy donors by centrifugation over a Ficoll-pague (GE-healthcare) gradient. Monocytes were isolated from PBMC by positive selection of CD14+ cells by magnetic beads (Dynal, Invitrogen) according to the manufacturer's instructions. The CD14+ monocytes were cultured in 6-well plates in RPMI/2% Human AB Serum recombinant human recombinant granulocyte-macrophage colony-stimulating factor (GM-CSF, 20 ng/ml) and IL-4 (20 ng/ml)(PeproTech) for 6 days, replenishing the medium/cytokines after 2 and 5 days. After 6 days of culture the immature DCs are re-cultured into 96-well plates in a concentration of $1 \times 10^6$ cells/ml and left untreated or treated with a cocktail and/or hBD2 for a further 24 h. hBD2 was tested in four concentrations in quadruplicate. hBD2 was analyzed for its ability to suppress hDC-maturation into a proinflammatory phenotype using a proinflammatory cocktail that contained LPS (100 ng/ml) and IFN-γ (20 ng/ml). Dexamethasone was added 20 h prior to the cocktail as positive control for a compound with proven clinical anti-inflammatory activity. The incubation with hBD2 was done 4 h prior to addition of cocktail.

Cytokine ELISA

Cell culture supernatants were collected and stored at −80° C. Amounts of IL-23 was measured by standard sandwich ELISA using commercially available antibodies and standards according to the manufacturer's protocols (eBioscience).

MTT Assay

A MTT based cell growth determination kit was used as a measure of cell survival after 48 h in order to evaluate if any of the cells were severely affected by treatment with vehicles, cocktail or hBD2 and was done according to the manufacturer's protocols (Sigma).

Statistical Analyses

All experiments were performed at least twice, with representative results shown. The data presented are expressed as mean plus/minus standard deviation (SEM). Statistical significance was determined by 2-way ANOVA with the variables being treatment (hBD2, dexamethazone, ect.) and stimulation (LPS, LTA, peptidoglycan, ect.) followed by Bonferroni post-test as reported in the table legends. Differences were considered significant for $p < 0.05$.

Results

TABLE 24

IL-23 (pg/ml) in supernatants of human CD14+ monocyte-derived dendritic cells stimulated with either medium (unstimulated), or LPS and IFN-γ and treated with either medium (untreated), hBD2 or Dexamehtasone, average (SEM), N = 4, one representative donor out of three. *$p < 0.05$, $p < 0.01$, *$p < 0.001$ analyzed by 2-way ANOVA and compared to non-treated cells by Bonferroni posttests. nd: not detected (below detection limit).

| IL-23 pg/ml (SEM) | Unstimulated | LPS (100 ng/ml) and IFN-γ (20 ng/ml) |
|---|---|---|
| Untreated | 375 (96) | 3569 (130) |
| hBD2 1 μg/ml | nd | 3833 (88) |
| hBD2 10 μg/ml | 451 (121) | 3308 (169)* |
| hBD2 30 μg/ml | nd | 3042 (46)*** |
| hBD2 100 μg/ml | nd | 2145 (202)*** |
| Dexamethasone 1 μM | 424 (38) | 1147 (268)*** |

TABLE 25

IL-23 (pg/ml) in supernatants of human PBMC stimulated with either medium (control), 0.6 ng/ml LPS, 20 ng/ml LPS or 5 μg/ml LTA and treated hBD2, Dexamehtasone or Infliximab, average (SEM). *$p < 0.05$, $p < 0.01$, *$p < 0.001$ analyzed by 1-way ANOVA and compared to non-treated cells by Dunnett's Multiple Comparison posttest.

| IL-23 pg/ml (SEM) | Control | LPS 0.6 ng/ml | LPS 20 ng/ml | LTA 5 μg/ml |
|---|---|---|---|---|
| Control (non-treated) | 257 (7) | 553 (6) | 510 (5) | 762 (20) |
| hBD2 1 μg/ml | 218 (5) | 338 (10)** | 263 (5)** | 383 (20)** |
| hBD2 10 μg/ml | 211 (4) | 462 (2)* | 295 (1)** | 438 (9)** |
| hBD2 100 μg/ml | 207 (4) | 484 (7) | 488 (8) | 810 (30) |
| Dexamethasone 3.5 ng/ml | 222 (5) | 202 (5)** | 192 (1)** | 223 (1)** |
| Infliximab 1 μg/ml | 227 (10) | 356 (10)** | 373 (2)** | 349 (1)** |

As shown in Table 24, hBD2 suppresses significantly and dose-dependently IL-23 secretion from human CD14+ monocyte-derived dendritic cells.

For human PBMC, IL-23 secretion was also significantly suppressed (Table 25). On these cells there was an inverse dose-dependency, that was found to be a bell-shaped dose-response inhibition curve when testing lower doses of hBD2 (data not shown).

This shows that hBD2 might have a suppressive effect in a cronic autoimmune condition by suppression of IL-23 secretion, as IL-23 is an important part of the inflammatory response. Th17 cells are dependent on IL-23 for their survival and expansion, and Th17 cells have been shown to be pathogenic in several autoimmune diseases, such as Crohn's disease, ulcerative colitis, psoriasis and multiple sclerosis.

Example 7

Reduction of TNF Secretion from PBMCs with Mouse Beta Defensin 3 (mBD3)

Example 7 was carried out essentially as described in Example 4 for human PBMCs. Mouse beta defensin 3 (mBD3) was prepared using the same protocol as was used for production of hBD2 in Example 1. The amino acid sequence of mBD3 is shown in SEQ ID NO:6. Mouse PBMCs were prepared as described below.

Isolation and Stimulation of Mouse Peripheral Blood Mononuclear Cells (PBMC)

Mouse peripheral blood mononuclear cells were isolated from blood of ten NMRI mice. In short, heparinized blood was diluted 1/1 v/v with RPMI and subjected to Ficoll density centrifugation within 2 h of drawing. Plasma was collected from the top and discarded. Isolated PBMC were resuspended in culture medium (RPMI 1640 (Gibco, 42401) w/1% penicillin and streptomycin and 1% L-Glutamine) and seeded in 96-well culture plates with 115.500 cells per well in a total of 200 µl. PBMC from the same donor were stimulated with 100,10 or 1 µg/ml of hBD2 or mBD3 (mouse beta defensin 3); either alone or together with 20 ng/ml LPS (E. coli, O111:B4, Sigma L4391). Dexamethasone was added at 3.5 ng/ml to cultures with and without LPS stimulation. The supernatants were collected after incubation at 37° C. for 24 hours, and stored at −80° C. until cytokine measurement.

Cytokine production in supernatants was measured by flow cytometry with a mouse inflammation cytometric bead array (CBA) according to manufacturer's instructions (BD) on a FACSarray flow cytometer.

Viability was measured by Alamar Blue (Biosource DALL 1100) after supernatant were collected.

Results

TABLE 26

TNF production from human peripheral blood mononuclear cells (PBMC) after treatment with LPS with and without hBD2, all samples tested on the same donor, representative experiment out of two donors. TNF measured by Cytometric Bead Array (CBA) on a FACSarray, ***$p < 0.001$ compared to respective control, analysed by 2-way ANOVA (N = 2).

| TNF pg/ml (SEM) | Medium | LPS 20 ng/ml |
|---|---|---|
| Medium | 5 (1) | 1353 (140) |
| mBD3 1 µg/ml | 2 (0) | 384 (11)*** |
| mBD3 10 µg/ml | 2 (0) | 51 (1)*** |
| mBD3 100 µg/ml | 39 (19) | 166 (17)*** |
| hBD2 1 µg/ml | 3 (0) | 633 (110)*** |
| hBD2 10 µg/ml | 2 (0) | 359 (10)*** |
| hBD2 100 µg/ml | 2 (0) | 342 (34)*** |
| Dexamethasone 3.5 ng/ml | 1 (0) | 460 (29)*** |
| Infliximab 1 µg/ml | 0 (0) | 1 (0)*** |

TABLE 27

TNF production from mouse peripheral blood mononuclear cells (PBMC) after treatment with LPS with and without mBD3, all samples tested on the same donor, representative experiment out of two donors. TNF measured by Cytometric Bead Array (CBA) on a FACSarray, ***$p < 0.001$ compared to respective control, analysed by 2-way ANOVA (N = 2).

| TNF pg/ml (SEM) | Medium | LPS 20 ng/ml |
|---|---|---|
| Medium | 578 (3) | 2063 (77) |
| mBD3 1 µg/ml | 347 (32) | 1600 (47)*** |
| mBD3 10 µg/ml | 180 (0) | 297 (9)*** |
| mBD3 100 µg/ml | 182 (5) | 195 (6)*** |
| Dexamethasone 3.5 ng/ml | 94 (3) | 328 (8)*** |
| Infliximab 1 µg/ml | 530 (4) | 2119 (31) |

As shown in Table 26, mouse beta defensin 3 (mBD3) is downregulating the secretion of TNF from human PBMCs to the same extend as hBD2 and dexamethason. mBD3 also downregulate the secretion of TNF from mouse PBMC (Table 27).

Accordingly, in this setup, mBD3 exhibits excellent anti-inflammatory activity.

REFERENCES

Bonoiotto M., W J Jordan, J. Eskdale, A. Tossi, N. Antcheva, S. Crovella, N D Connell and G Gallagher. Human β-Defensin 2 Induces a Vigorous Cytokine Response in Peripheral Blood Mononuclear Cells. *Antimicrobial Agents and Chemotherapy* (2006), 50, 1433-1441.

Bowdish et al., Immunomodulatory properties of defensins and cathelicidins. *Curr. Top. Microbiol. Immunol.* (2006) 306, 27-66.

Gersemann et al., Crohn's disease-defect in innate defence. *World J. Gastroenterol.* (2008) 14, 5499-5503.

Lehrer R. I., Primate defensins. *Nat. Rev. Microbiol.* (2004) 2, 727-738.

Swidsinski et al., Mucosal flora in inflammatory bowel disease. *Gastroenterology* (2002) 122, 44-54.

Niyonsaba F., H. Ushio, N. Nakano, W. Ng, K. Sayama, K. Hashimoto, I. Nagaoka, K. Okumura and H. Ogawa. Antimicrobial peptides human β-defensins stimulate epidermal keratinocyte migration, proliferation and production of proinflammatory cytokines and chemokines. *Journal of Investigative Dermatology* (2007), 127, 594-604.

Rowland T L, S M McHugh, J Deighton, R J Dearman, P W Ewan and I Kimber. Differential regulation by thalidomide and dexamethasone of cytokine expression in human peripheral blood mononuclear cells. *Immunopharmacology* (1998), 40, 11-20.

Wang et al., Host-microbe interaction: mechanisms of defensin deficiency in Crohn's disease. *Expert. Rev. Anti. Infect. Ther.* (2007) 5, 1049-1057.

Wehkamp et al., Reduced Paneth cell alpha-defensins in ileal Crohn's disease. *Proc. Natl. Acad. Sci. U.S.A* (2005) 102, 18129-18134.

Reference to a Sequence Listing

This application contains a Sequence Listing in computer readable form.

The computer readable form is incorporated herein by reference.

The invention claimed is:

1. A method of treating an inflammatory bowel disease, comprising administering parenterally to a subject in need of such treatment an effective amount of a beta-defensin comprising an amino acid sequence that has at least 95% identity to the amino acid sequence of SEQ ID NO:2.

2. The method of claim 1, wherein the effective amount is effective to reduce TNF-alpha activity in the treated tissues.

3. The method of claim 1, wherein the beta-defensin is administered subcutaneously or intravenously.

4. The method of claim 1, wherein the beta-defensin is administered at a daily dosage of from about 0.001 mg/kg body weight to about 10 mg/kg body weight.

5. The method of claim 1, wherein the beta-defensin is administered at a daily dosage of from about 0.01 mg/kg body weight to about 10 mg/kg body weight.

6. The method of claim 1, wherein the beta defensin comprises conserved cysteine residues corresponding to amino acid positions 8, 15, 20, 30, 37, 38 of SEQ ID NO: 2.

7. The method of claim 1 wherein any amino acid substitution in the beta defensin relative to SEQ ID NO: 2 is a conservative substitution.

8. A method of treating an inflammatory bowel disease, comprising administering parenterally to a subject in need of such treatment an effective amount of a beta-defensin comprising the amino acid sequence of SEQ ID NO:2.

* * * * *

SEQUENCE LISTING

<160> NUMBER OF SEQ ID NOS: 6

<210> SEQ ID NO 1
<211> LENGTH: 36
<212> TYPE: PRT
<213> ORGANISM: Homo sapiens
<220> FEATURE:
<221> NAME/KEY: mat_peptide
<222> LOCATION: (1)..(36)

<400> SEQUENCE: 1

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 2
<211> LENGTH: 41
<212> TYPE: PRT
<213> ORGANISM: Homo sapiens
<220> FEATURE:
<221> NAME/KEY: mat_peptide
<222> LOCATION: (1)..(41)

<400> SEQUENCE: 2

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
        35                  40

<210> SEQ ID NO 3
<211> LENGTH: 45
<212> TYPE: PRT
<213> ORGANISM: Homo sapiens
<220> FEATURE:
<221> NAME/KEY: mat_peptide
<222> LOCATION: (1)..(45)

<400> SEQUENCE: 3

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Thr Gly Lys
            20                  25                  30

Cys Ser Thr Arg Gly Arg Lys Cys Cys Arg Arg Lys Lys
        35                  40                  45

<210> SEQ ID NO 4
<211> LENGTH: 50
<212> TYPE: PRT
<213> ORGANISM: Homo sapiens
<220> FEATURE:
<221> NAME/KEY: mat_peptide
<222> LOCATION: (1)..(50)

<400> SEQUENCE: 4

Glu Phe Glu Leu Asp Arg Ile Cys Gly Tyr Gly Thr Ala Arg Cys Arg
1               5                   10                  15

Lys Lys Cys Arg Ser Gln Glu Tyr Arg Ile Gly Arg Cys Pro Asn Thr
            20                  25                  30

```
Tyr Ala Cys Cys Leu Arg Lys Trp Asp Glu Ser Leu Leu Asn Arg Thr
        35                  40                  45

Lys Pro
    50

<210> SEQ ID NO 5
<211> LENGTH: 37
<212> TYPE: PRT
<213> ORGANISM: Artificial Sequence
<220> FEATURE:
<223> OTHER INFORMATION: hBD-4 variant consisting of amino acids 3-39
      of SEQ ID NO:4
<220> FEATURE:
<221> NAME/KEY: mat_peptide
<222> LOCATION: (1)..(37)

<400> SEQUENCE: 5

Glu Leu Asp Arg Ile Cys Gly Tyr Gly Thr Ala Arg Cys Arg Lys Lys
1               5                   10                  15

Cys Arg Ser Gln Glu Tyr Arg Ile Gly Arg Cys Pro Asn Thr Tyr Ala
            20                  25                  30

Cys Cys Leu Arg Lys
        35

<210> SEQ ID NO 6
<211> LENGTH: 40
<212> TYPE: PRT
<213> ORGANISM: Mus musculus
<220> FEATURE:
<221> NAME/KEY: mat_peptide
<222> LOCATION: (1)..(40)

<400> SEQUENCE: 6

Lys Ile Asn Asn Pro Val Ser Cys Leu Arg Lys Gly Gly Arg Cys Trp
1               5                   10                  15

Asn Arg Cys Ile Gly Asn Thr Arg Gln Ile Gly Ser Cys Gly Val Pro
            20                  25                  30

Phe Leu Lys Cys Cys Lys Arg Lys
        35                  40
```